(12) United States Patent
Bell

(10) Patent No.: US 6,342,492 B1
(45) Date of Patent: *Jan. 29, 2002

(54) ANTI-VIRAL TRIAZA COMPOUNDS AND COMPOSITIONS

(75) Inventor: Thomas W. Bell, Reno, NV (US)

(73) Assignee: The Research Foundation of State University of New York, Albany, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/894,491

(22) PCT Filed: Feb. 16, 1996

(86) PCT No.: PCT/US96/02132

§ 371 Date: Aug. 7, 1997

§ 102(e) Date: Aug. 7, 1997

(87) PCT Pub. No.: WO96/25167

PCT Pub. Date: Aug. 22, 1996

Related U.S. Application Data

(63) Continuation-in-part of application No. 08/392,550, filed on Feb. 17, 1995, now Pat. No. 5,663,161.

(51) Int. Cl.$^7$ ........................ A01N 43/00; A01N 43/66; C07D 255/02
(52) U.S. Cl. ................ 514/183; 514/246; 540/474
(58) Field of Search ................. 514/183, 246; 540/474

(56) References Cited

U.S. PATENT DOCUMENTS

| 4,001,212 A | 1/1977 | Richman .............. 260/739 BC |
| 4,994,560 A | 2/1991 | Kruper, Jr. et al. ........... 534/10 |
| 5,021,409 A | 6/1991 | Murrer et al. .............. 514/183 |
| 5,284,644 A | 2/1994 | Kruper, Jr. et al. ........ 424/1.53 |
| 5,322,681 A | 6/1994 | Klaveness ..................... 424/9 |

FOREIGN PATENT DOCUMENTS

| JP | 8 027 129 | 1/1996 |
| WO | WO 93 12096 | 6/1993 |
| WO | WO 93 12097 | 6/1993 |

OTHER PUBLICATIONS

H–J Choi, Ph.D. Dissertation: Synthesis And Properties of Polycyclic Triamines And Application of Ionophores to Ion–Selective Electrodes, State University of New York at Stony Brook, 1989.

E. DeClercq, et al., "Highly Potent and Selective Inhibition of Human Immunodeficiency Virus by the Bicyclam Derivative JM3100", *Antimicrobial Agents And Chemotherapy* 38(4):668–674 (Apr. 1994).

J.C. Barrish, et al. "Antiviral Agents" in *Annual Reports in Medicinal Chemistry* 28, Academic Press, Inc., 1993, 131–140.

R.F. Schinazi, et al. "Insights Into HIV Chemotherapy," *Aids Research and Human Retroviruses* 8(6):963–990 1992.

*Primary Examiner*—Russell Travers
(74) *Attorney, Agent, or Firm*—Hoffmann & Baron, LLP

(57) ABSTRACT

The invention relates to a family of new synthetic triamine compounds which can be used in antiviral pharmaceutical compositions.

15 Claims, No Drawings

ANTI-VIRAL TRIAZA COMPOUNDS AND COMPOSITIONS

This application is a 371 of PCT/US96/02132 filed Feb. 16, 1996 which is a continuation-in-part of U.S. application 08/392,550 filed Feb. 17, 1995 now issued U.S. Pat. No. 5,663,161.

The invention relates to a family of new synthetic triamine compounds which can be used in pharmaceutical compositions such as antivirals.

BACKGROUND OF THE INVENTION

The number of biologically active compounds useful as antivirals is very limited. Particularly limited are anti-HIV agents. Currently approved anti-HIV drugs include nucleoside analogs such as AZT. Unfortunately, recent results of a European trial of AZT in asymptomatic HIV-infected persons showed that administration of the drug caused no difference in survival after three years. In the face of slow progress on the development of an effective AIDS vaccine, a National Task Force on AIDS Drug Development has been established to explore new approaches to AIDS chemotherapy.

It is unlikely that a cure for AIDS will be discovered because HIV integrates itself into the host's genome and the main strategy to combat the disease is to keep the HIV virus from proliferating. At least 16 steps in the HIV life cycle have been identified as possible points for therapeutic intervention, yet all of the anti-HIV drugs licensed in the U.S. so far (AZT, ddI and ddC) are nucleoside inhibitors of HIV reverse transcriptase (RT). Rapid mutation of the virus presents a key challenge to antiretroviral drug therapy and AZT-resistant strains of HIV appear in patients after prolonged treatment. Non-nucleoside RT inhibitors are currently under investigation, but it is expected that combinations of drugs operating by different mechanisms will combat viral resistance most successfully. Hence, there is an urgent search for new drugs acting at different stages in the HIV life cycle. More recently discovered anti-HIV agents include certain bicyclams and quinolines such as quinoline-4-amine. The mechanism of action of the quinoline compound is unknown, but the bicyclams are reported to be inhibitors of HIV uncoating.

Another type of compound, the triaza macrocycles, have been used primarily for metal complexation. Previously, no biological activity has been suggested for these compounds.

SUMMARY OF THE INVENTION

The present invention provides a family of triaza compounds which show antiviral properties for use against a number of viruses including HIV-1 and HIV-2.

The basic structure of the compounds is represented by formula I:

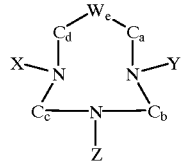

formula I wherein

W represents a bridge carbon which is additionally bonded to at least one polar or non-polar side group substituent selected from the group consisting of double-bonded carbon, double bonded oxygen, hydroxyl, alkyl of about one to 10 carbons, alkoxy of about one to 10 carbons, aryl of about 7 to 10 carbons, a halogen, methyl halogen, methylene halide, epoxide (or oxirane), acyl, $CH_2OH$ and hydrogen; halogen is F, Cl, I or Br; halide is $F_2$, $Cl_2$, $I_2$ or $Br_2$.

X and Y independently represent an aromatic group, an alkyl group, a sulfonyl group or a carbonyl group said aromatic group selected from the group consisting of Ar, Ar sulfonyl, Ar carboxy and Ar alkyl where Ar is an aromatic cyclic or heterocyclic ring having from five to seven members. The alkyl group which may be present for X and Y or as a substituent on Ar has from one to ten carbons. X and Y are not both an alkyl group. Preferably at least one of X or Y is an aromatic group.

Z represents a group listed for X and Y or a fused aryl moiety; said aryl moiety having from seven to ten carbons. Z may also represent hydrogen.

a and d independently represent a number from zero to 10; b and c independently represent a number from one to 10; and e represents a number from zero to three; and preferably, $a+d+e \geq 1$. Formula I represents a cyclic or acyclic structure and contains sufficient hydrogens for a stable molecule. Moieties for $C_a$ and $C_d$ can include double bonds particularly when the structure for formula I is acyclic.

In one preferred embodiment, W is ethene, X and Y are tosyl, Z is benzyl or —$COR^2$, a, d, and e are one, and b and c are three.

The compounds of formula I have antiinfective activity and have a range of uses including as a pharmaceutical agent for use in the prevention and chemoprophylaxis of viral illnesses. The compounds can also be used as an antiinfective or antiseptic as a coating or additive on articles such as medical devices, contraceptives, dressings, and in blood product preparations and similar biologicals.

A method of inhibiting a virus comprises contacting the virus, a virus-containing milieu, a virus-infectable cell or a virus-infected cell with a virus-inhibiting amount of the compound of formula I.

DETAILED DESCRIPTION

The compounds are characterized as having at least three nitrogen atoms (amine sites) linked by at least two alkylene bridges or linking groups to form triamines. The alkylene bridge linking groups are preferably alkanes containing from one to ten carbons.

The triamines may be formed into a triazamacrocycle by a third alkylene bridge which is preferably alkane having from one to ten carbons connecting the two end nitrogens of the triamine compound.

The alkylene bridges linking the nitrogen atoms can additionally include aromatic or non-aromatic rings fused to the alkylene bridge. Bridges containing fused rings and linking two nitrogens of the triamine structure may be exemplified by the following:

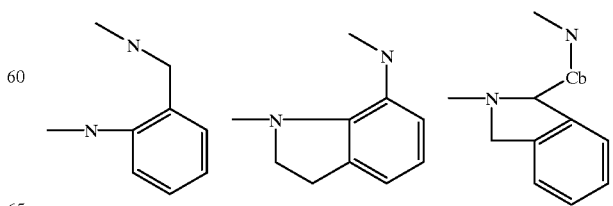

The alkylene bridges are preferably —(CH$_2$)$_3$—.

The bridge carbon (designated W) of the third alkylene bridge may be functionalized with (i.e., bonded to) a side substituent which is a polar group.

Representative groups for W include

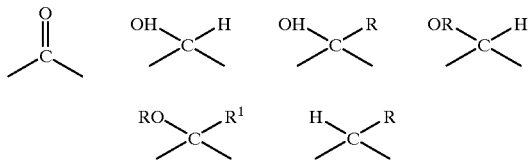

(R and R$^1$ are alkyl of 1–10 carbons),

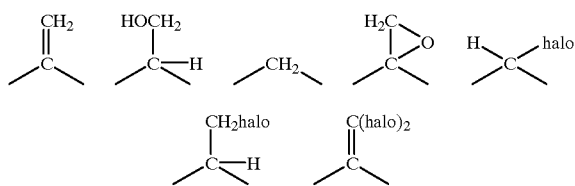

(halo is F, Cl, Br or I). W may also be unfunctionalized, i.e., bonded to hydrogen. W is preferably

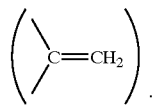

X and Y are independently an aromatic, alkyl, sulfonyl or carbonyl group or hydrogen. Representative aromatic groups include five or six membered rings which may have heteroatoms of nitrogen, oxygen or sulfur. The rings include, for example, phenyl, pyrrolyl, furanyl, thiophenyl, pyridyl, thiazoyl, etc. The aromatic group (Ar) for X and Y may be substituted with a hydrophilic group. Preferably the Ar is substituted with NO, NO$_2$, NH$_2$, NHR, NHR$_2$, OH, OR, SH, SR, SOR, SO$_3$R, halo, C(halogen)$_3$

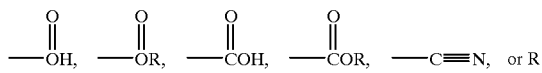

where R is alkyl of one to 10 carbons; R is preferably alkyl of one to three carbons; R is more preferably methyl. The aromatic groups are more preferably further substituted with sulfonyl, carboxy, alkyl of one to 10 carbons or amino. Representative of groups for X and Y are

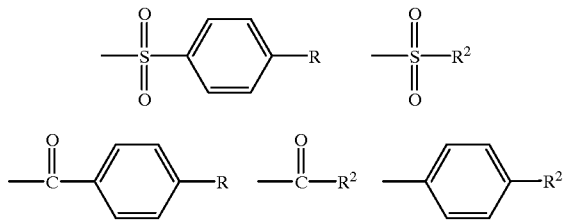

where, e.g., R is alkyl of 1 to 10 carbons, and R$^2$ is amino, nitro, sulfhydryl, hydroxy, alkoxy of one to three carbons, acetamino or methyl.

The alkyl groups for X and Y may be branched or unbranched and include up to ten carbons. Typical examples of alkyl groups for X and Y include methyl, ethyl, n-propyl, isopcropcyl, n-butyl, sec-butyl-, tert-butyl, isobutyl, pentyl, hexyl, heptyl, octyl, nonyl and decyl. The alkyl groups may be in whole or in part in the form of rings such as cyclopentyl, cyclohexyl, cycloheptyl and cyclohexylmethyl. The cyclic groups may be further substituted with alkyl or aryl groups.

Preferably, X and Y both contain aromatic groups. More preferably, X and Y are both tosyl:

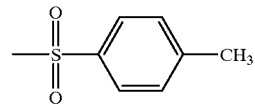

The groups for Z are the same as for X and Y or a fused aryl moiety. Fused rings for the Z position include naphthalene, phenanthrene, anthracene, indole, quinoline, isoquinoline, carbazole, benzimidazole and benzofuran. Z is preferably an unfused group, more preferably benezyl.

All groups for W, X, Y and Z may be further substituted with polar substituents such as NF$_2$, NO, NO$_2$, SH, SO$_3$H, OH, and CO$_2$H. These polar groups are capable of aiding solubility of the compounds.

Representative compounds include
3-Methylene-1,5-ditosyl-1,5,9-triazacyclododecane
5,9-Ditosyl-7-hydroxymethyl-1,5,9-tri-azabicyclo-[5,5,0]tridecane
5,9-Ditosyl-13-oxa-1,5,9-triazatricyclo[5,5,1$^{1.7}$, 1$^{7,12}$]-tetradecane
9-Benzyl-3-hydroxymethyl-1,5-ditosyl-1,5,9-triazacylododecane
9-Benzyl-3-chloromethyl-1,5-ditosyl-1,5,9-triazacyclododecane
3-Chloromethyl-1,5-ditosyl-1,5,9-triazacyclododecane
N,N-bis(3-toluenesulfonamidopropyl) toluenesulfonamide
1,5,9-Tritosyl-1,5,9-triazacyclododecane
3-Methylene-1,5,9-tritosyl-1,5,9-triazacyclododecane
3-Hydroxymethyl-1,5,9-tritosyl-1,5,9-triazacyclododecane
3-Chloromethyl-1,5,9-tritosyl-1,5,9-triazacylododecane
11-Methylene-1,5,9-triazabicyclo[7,3,3]pentadecane
1,5,9-Triazabicyclo[9,1,1]tridecane
9-Benzyl-3-keto-1,5-ditosyl-1,5,9-triazacyclododecane
9-Benzyl-3-methyl-1,5-ditosyl-1,5,9-triazacyclododecane
9-Benzyl-3-methylene-1,5-ditosyl-1,5,9-triazacyclododecane-9-oxide
9-Acyl-3-methylene-1,5-ditosyl-1,5,9-triazacyclododecane
9-Alkyl-3-methylene-1,5-ditosyl-1,5,9-triazacyclododecane
9-Acyl-3-methylene-1,5-ditosyl-1,5,9-triazacyclododecane epoxide
9-Benzyl-1-formyl-3-methylene-1,5,9-triazacyclododecane
9-Benzyl-1-formyl-3-methylene-5-tosyl-1,5,9-triazacyclododecane
9-Benzyl-3-methylene-1-tosyl-1,5,9-triazacyclododecane
9-Benzyl-3-methylene-1-acyl-5-tosyl-1,5,9-triazacyclododecane
9-(Ethoxycarbonyl)-3-methylene-1,5-ditosyl-1,5,9-triazacyclododecane
N-Benzylbis(3-benzenesulfonamidopropyl)amine
9-Benzyl-3-methylene-1,5-dibenzenesulfonyl-1,5,9-triazacyclododecane
N-Benzylbis[3-(N'-2-propenyltoluenesulfonamido) propyl] amine dihydrogen sulfate
N-Benzyl-N-[3-(N'-2-methyl-2-propenyl-toluenesulfonamido)propyl]-N-(3-toluenesulfonamido-propyl)amine dihydrogen sulfate
N-Benzylbis[3-(N'-2-methyl-2-propenyltoluene-sulfonamido)propyl]amine dihydrogen sulfate.

The compounds of this invention possess valuable pharmacological properties for both human and veterinary medicine. The compounds display antiviral and antitumor effects and are useful particularly in the prevention and chemoprophylaxis of viral illnesses.

The compounds can also be used in vitro and employed in admixture with carriers, germicides, fungicides, or soaps, etc., for use as antiseptics solutions and the like, particularly in conjunction with hospital housekeeping procedures to combat viruses such as herpes and HIV. They are also useful as intermediates in the production of other polyamine drugs by the method of U.S. Pat. No. 5,021,409 and in the synthesis of metal chelating compounds, e.g., by methods of Bradshaw et al., *Aza-Crown Macrocycles*, Wiley, New York, 1993.

The pharmacologically active compounds of this invention can be processed in accordance with conventional methods of pharmacy to produce medicinal agents for administration to patients, e.g., mammals including humans. The pharmacological compounds of the invention are generally administered to animals, including but not limited to mammals and avians; more preferably to mammals including humans, primates and avians including poultry.

The compounds of this invention can be employed in admixture with conventional pharmaceutically acceptable diluents, excipients, carriers and other components such as vitamins to form pharmaceutical compositions.

Pharmaceutical compositions may be prepared by known principles for parenteral, enteral and topical application. Preferably, the administration is parenteral.

Generally, the compounds of this invention are dispensed in unit dosage form comprising 10 to 1000 mg in a pharmaceutically acceptable carrier per unit dosage. The dosage of the compounds according to this invention generally is about 0.1 to 110 mg/kg body weight/day preferably 0.1 to 20 mg/kg/day when administered to patients, e.g., humans to treat viral infections such as HIV.

Viruses share certain common characteristics; they consist of a nucleic acid genome which may be double-stranded DNA, single stranded DNA, single-strand positive RNA, single-strand negative RNA and double-stranded RNA. The nucleic acid is surrounded by protective protein shell (capsid) and the protein shell may be enclosed in an envelope which further includes a membrane.

The treatment of viral disease has been approached by inhibiting absorption or penetration of virus into cells, inhibiting intracellular processes which lead to the synthesis of viral components, or inhibition of release of newly synthesized virus from the infected cell. The inhibition of one or more of these steps depends on the chemistry or mode of action of the virus.

The compounds of the invention have been shown to have antiviral effect against various viruses including retroviruses, particularly HIV which researchers believe to be a positive strand RNA virus. Effectiveness has also been shown against other viruses which infect humans including cytomegalovirus and herpesvirus which are believed to be double strand DNA viruses, influenza virus which is believed to be a negative strand RNA virus, and also rous sarcoma virus which infects avians. The invention will be illustrated by the following non-limiting examples.

I.A. Synthesis of Compounds 1 and 2

The synthesis of N-benzylbis(3-toluene-sulfonamidopropyl)amine (compound 2) and 9-benzyl-3-methylene-1,5-ditosyl-1,5,9-triazacyclodecane (CADA) (compound 1) is shown in Scheme 1.

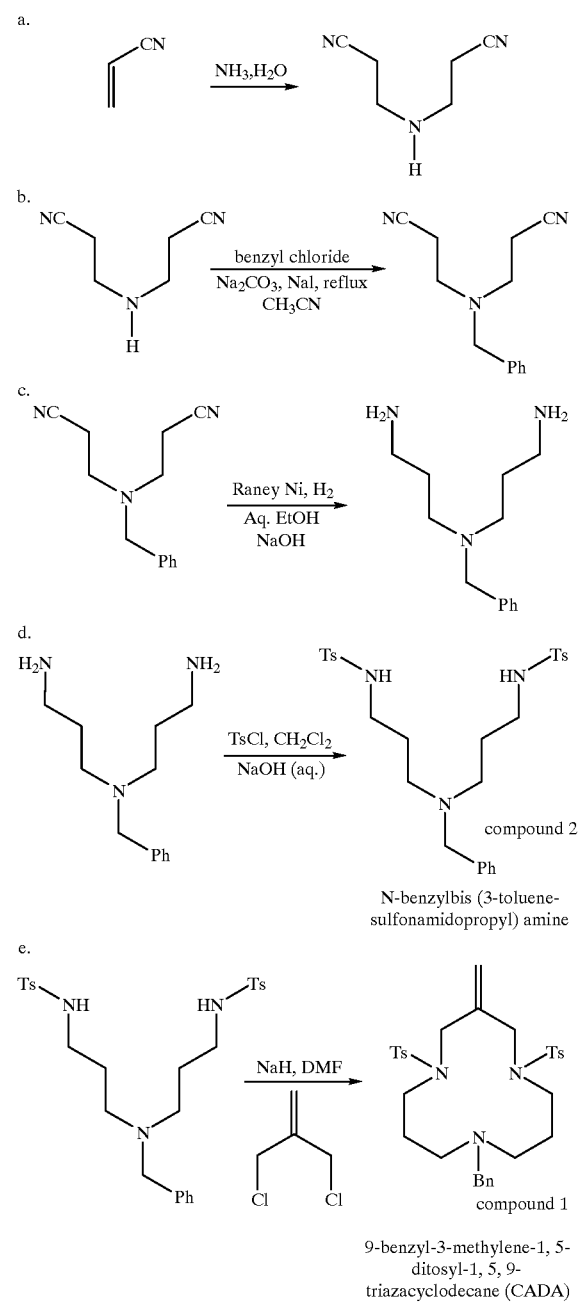

a. Bis(2-cyanoethyl)amine

Into a 1-L three-necked round-bottomed flask equipped with an addition funnel, a dry-ice/acetone-cooled Dewar condenser, thermometer, and nitrogen inlet, was added 354 g (6.7 mol) of acrylonitrile. The addition funnel was charged with 208 mL (3.2 mol) of concentrated ammonium hydroxide, the apparatus was flushed with nitrogen and the acrylonitrile was preheated to 70–75° C. by means of an 80° C. oil bath. The ammonium hydroxide was added dropwise to the vigorously stirred reaction mixture over a period of 2 h. Afterwards, the reaction mixture was stirred without external heating for 30 min., then heated to 70–75° C. by means of a 75° C. oil bath for an additional 30 min. The excess acrylonitrile and most of the water were removed by rotary evaporation and the residue was dried to constant weight under vacuum (0.5 mm Hg). The resulting yellow oil (387 g, 99%) was sufficiently pure to be used directly in the next step, but can be distilled under vacuum, bp 186–190° C. (15 mm). $^1$H NMR (CDCl$_3$) δ2.86 (t, J=6.6 Hz, 4 H), 2.44 (t, J=6.6 Hz, 4 H), 1.5 (br, 1 H). $^{13}$C NMR (CDCl$_3$) δ118.4, 44.4, 18.8. IR (film, cm$^{-1}$) 3330 (s), 2920 (s), 2850 (s), 2240 (s), 1440 (s), 1415 (s) 1360 (m), 1130 (s), 750 (br).

b. N-Benzylbis(2-cyanoethyl)amine

A mixture of 50.0 g (0.406 mol) of bis(2-cyanoethyl) amine, 51.45 g (0.406 mol) of benzyl chloride, 1.0 g (6.7 mmol) of sodium iodide, 22.05 g (0.208 mol) of sodium carbonate and 150 mL of acetonitrile was stirred mechanically and heated at reflux under nitrogen for 5 h. The cooled reaction mixture was filtered and the solids were washed with acetonitrile (3×50 mL). The combined filtrates were concentrated by rotary evaporation. A solution of the residue in 100 mL of CH$_2$Cl$_2$ was washed with saturated aqueous Na$_2$S$_2$O$_3$ (2×20 mL) and saturated aqueous NaCl (2×50 mL). The combined aqueous layers were extracted with CH$_2$Cl$_2$ (3×30 mL). The combined CH$_2$CO$_2$ solutions were dried over MgSO$_4$, filtered and concentrated by rotary evaporation. The residual solvent was removed under vacuum (0.5 mm), yielding 70.4 g (89%) of product as a light yellow oil. $^1$H NMR (CDCl$_3$/TMS) δ 7.34 (m, 5 H), 3.70 (s, 2 H), 2.88 (t, J=6.8 Hz, 4 H), 2.44 (t, J=6.8 Hz, 4 H). $^{13}$C NMR (CDCl$_3$) δ137.5, 128.3, 127.4, 118.4, 57.7, 49.1, 16.4. IR (film, cm$^{-1}$) 3070 (w), 3050 (m), 3020 (s), 2930 (s), 2830 (s), 2240 (s), 1595 (m), 1575 (w), 1485 (s), 1445 (s), 1415 (s), 1360 (br), 1250 (br), :1125 (s), 1070 (s), 1020 (s), 960 (s), 730 (s), 690 (s).

c. N-benzylbis(3-aminopropyl)amine

A mixture of 43.3 g (0.203 mol) of N-benzylbis(2-cyanoethyl)amine, 7.8 g of a 50% aqueous slurry of Raney nickel and 90 mL of a 1.4 M solution of NaOH in 95% ethanol was hydrogenated in a Parr apparatus for 48 h. The catalyst was removed by filtration and washed with 80 mL of 95% ethanol. The combined filtrates were concentrated by rotary evaporation. A solution of the residue in 100 mL of hexane/chloroform (1:1, v/v) was dried over Na$_2$SO$_4$, filtered and concentrated by rotary evaporation. Removal of solvent residues under vacuum (0.5 mm) afforded 40.3 g (90%) of product as a yellow oil. $^1$H NMR (CDCl$_3$/TMS) δ7.31 (m, 5 H), 3.52 (s, 2 H), 2.70 (t, J=6.8 Hz, 4 H), 2.45 (t, J=6.8 Hz, 4 H), 1.60 (quint., J=6.8 Hz, 4 H), 1.26 (s, 4 H). $^{13}$C NMR (CDCl$_3$) δ139.5, 128.3, 127.7, 126.3, 58.3, 50.9, 40.0, 30.6. IR (film, cm$^{-1}$) 3360 (br), 3270 (br), 3070 (w), 3050 (w), 3020 (m), 2920 (br. s), 2850 (s), 2800 (s), 1600 (s), 1485 (s), 1450 (s), 1360 (m), 1110 (br), 1070 (m), 1020 (m) 730 (m), 690 (m).

d. N-Benzylbis(3-toluenesulfonamidopropyl)amine (compound 2)

A solution of p-toluenesulfonyl chloride (20 g, 105 mmol) in 50 mL of CH$_2$Cl$_2$ was added dropwise with vigorous stirring over 2 h to a solution of N-benzylbis(3-aminopropyl)amine (11.07 g, 50 mmol) and NaOH (4.4 g, 110 mmol) in 30 mL of water. After stirring for an additional hour, the organic layer was separated, washed with equal volume of brine, dried over MgSO$_4$, and concentrated by rotary evaporation. Attempts to crystallize the crude oily product were not successful. All remaining solvent was removed under high vacuum and the product (25.1 g, 95%) was used without further purification. $^1$H NMR (CDCl$_3$/TMS) δ7.70 (d, J=8.2 Hz, 4 H, TsH$^{2,6}$), 7.28 (d, J=8.2 Hz, 4 H, TsH$^{3,5}$), 7.24 (m, 5 H, Ph), 5.80 (br, 2 H, NH), 3.43 (s, 2H, PhCH$_2$), 2.92 (t, J=6.2 Hz, 4 H, Ts-NCH$_2$), 2.45 (m, 4 H, Bn-N-CH$_2$), 2.42 (s, 6 H, TsCH$_3$), 1.64 (quint., J=6.3 Hz, 4 H, NCH$_2$CH$_2$). $^{13}$C NMR (CDCl$_3$) δ143.1, 136.9, 129.6, 129.0, 128.4, 127.3, 127.0, 58.6, 51.8, 42.2, 25.9, 21.4. IR (film, cm$^-$) 3280, 3050, 3020, 2940, 2850, 2810, 1595, 1490, 1450, 1320, 1150, 1085, 810, 730, 690, 660.

The compound 9-benzyl-3-methylene-1,5-ditosyl-1,5,9-triazacyclodecane (CADA) (compound 1) was synthesized in the following manner.

e. 9-Benzyl-3-methylene-1,5-ditosyl-1,5,9-triazacyclododecane (CADA) (compound 1)

Sodium hydride (3.6 g, 144 mmol, washed with hexane prior to use) was added under nitrogen to a solution of the product of procedure d., N-benzylbis(3-toluenesufonamidopropyl)amine (26.5 g, 50 mmol) in 500 mL of DMF. The mixture was held at 80–100° C. for 1 h then cannulated through a glass filter under N$_2$ into a 2-L three-necked round-bottomed flask equipped with a rubber septum, a thermometer, and an inlet for N$_2$. An additional 500 mL of DMF was used to insure complete transfer. The solution was stirred at 100° C. as a separate solution of 3-chloro-2-chloromethyl-1-propene (6.25 g, 50 mmol) in 50 mL of DMF was added over 9 h by means of a syringe pump. Upon completion of the addition, stirring at 100° C. under N$_2$ was continued an additional 12 h. The solvent was removed completely on a rotary evaporator using a hot water bath. A solution of the residue in 150 mL of CHCl$_3$ was washed with water, dried over MgSO$_4$ and concentrated by rotary evaporation. A solution of the resulting sticky, yellow crude product in a minimum volume of hot toluene was mixed with hexane to precipitate side-products. The supernatant solution was decanted and the residue was triturated with hexane several times. The combined supernatants were concentrated by rotary evaporation. The resulting residue was dried in vacuo and recrystallized from chloroform/ethanol, yielding CADA (16 g, 55%) as a white solid, mp 156–158° C. NMR (CDCl$_3$/TMS) δ7.66 (d, J=8 Hz, 4 H, TsH$^{2,6}$), 7.31 (d, J=8 Hz, 4 H, TSH$^{3,5}$), 7.20 (m, 5 H, Ph), 5.23 (s, 2 H, C=CH$_2$), 3.84 (s, 4 H, allylic), 3.39 (s, 2 H, PhCH$_2$), 3.12 (t, J=6.8 Hz, 4 H, Ts-NCH$_2$), 2.44 (s, 6 H, TsCH$_3$), 2.36 (t, J=6 Hz, 4 H, Bn-N-CH$_2$), 1.63 (quint., J=6 Hz, 4 H, NCH$_2$Cl$_2$). $^{13}$C NMR (CDCl$_3$) δ143.4, 139.3, 138.3, 135.5, 129.7, 128.7, 128.1, 127.2, 126.9, 116.2, 59.0, 51.0, 49.5, 44.0, 24.4, 21.5. IR (film, cm$^-$) 3020, 2940, 2920, 2850, 2800, 1600, 1490, 1450, 1330, 1150, 1080. Anal. calcd. for C$_{31}$H$_{39}$N$_3$S$_2$O$_4$: C, 64.00; H, 6.76; N, 7.22; S, 11.02. Found: C, 63.91; H, 6.65; N, 7.13; S, 11.04.

I.B. Synthesis of Compounds 210 and 211

210 N-Benzylbis(3-benzenesulfonamidopropyl)amine and 211 9-Benzyl-3-methylene-1,5-dibenzenesulfonyl-1,5,9-triazacyclododecane were synthesized as follows:

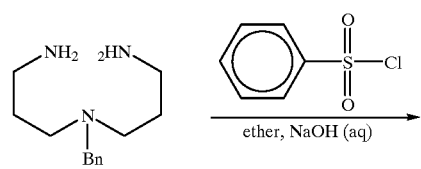

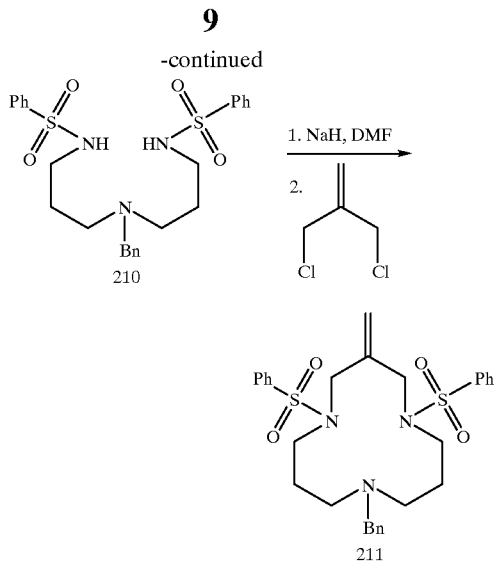

a. N-Benzylbis(3-benzenesulfonamidopropyl)amine (compound 210)

HCl Salt. Into a 1-L round-bottomed flask equipped with an addition funnel, a stirring bar and a nitrogen inlet, were added 40.2 g (0.23 mol) of benzenesulfonyl chloride, 150 mL of ether and 175 mL of a saturated aq. NaCl solution. The addition funnel was charged with a solution of 25.4 g (0.12 mol) of N-benzylbis(3-aminopropyl)amine and 175 mL of 1.3 N aq. NaOH. The amine was added dropwise with vigorous stirring over 2 h. The mixture was poured into a separatory funnel and the aqueous portion (bottom layer) removed. The two organic layers were diluted with 100 mL of chloroform and the resulting solution concentrated by rotary evaporation to a pale yellow oil. The residue was dissolved in 150 mL of dichloromethane. A solution of 2 N aq. HCl (60 mL) and 60 mL of saturated aq. NaCl was added and the mixture was stirred vigourously for 1 h. The layers were separated and the organic (lower) layer was washed with a saturated aq. NaCl solution (3×50 mL) and concentrated by rotary evaporation. The residue was recrystallized by bringing an ethanol solution of the residue to a boil and adding ethyl acetate to induce precipitation. The mixture was cooled to room temperature then to −25° C. for 2 weeks. Vacuum filtration of the precipitate gave 55.9 g (90%) of N-benzylbis(3-benzenesulfonamidopropyl)amine hydrochloride as a white solid. An analytical sample was prepared by drying at 65° C. (1 mm) for 13 h, mp 135–136° C. $^1$H NMR (DMSO-$d_6$) δ11.0 (br, 1 H, BnNH), 7.89 (t, 2 H, J=5.7 Hz, $SO_2$NH), 7.79 (d, 4 H, J=7.2 Hz, $SO_2ArH^{2,6}$), 7.59 (m, 8 H. $SO_2ArH^{3,4,5}$, BnArH$^{3,5}$), 7.41 (m, 3 H, BnArH$^{2,4,6}$) 4.23 (d, 2 H, J=4.2 Hz, PhCH$_2$N), 2.93 (m, 4 H, ArSO$_2$NCH$_2$CH$_2$), 2.74 (m, 4 H, BnNCH$_2$CH$_2$), 1.88 (m, 4 H, NCH$_2$CH$_2$CH$_2$N), $^{13}$C NMR (DMSO-$d_6$) (140.3, 132.6, 131.5, 129.8, 129.6, 129.4, 128.9, 126.6, 56.0, 49.4, 40.1, 23.3. IR (KBr, cm$^{-1}$) 3242 (br), 3073 (s), 2976 (m), 2855 (m), 2609 (s), 1470 (m), 1446 (s), 1330 (s), 1163 (s), 1092 (s), 740 (s), 689 (s). Anal. calc. for $C_{25}H_{31}N_3S_2O_4$ HCl; C, 55.80; H, 5.99; N, 7.81; S, 11.92; Cl, 6.59. Found: C, 55.47; H, 6.13; N, 7.63; S, 11.63; Cl, 6.92%.

Free base. In a round-bottomed flask equipped with a magnetic stir bar, 6.51 g (12.1 mmol) of N-benzylbis(3-benzenesulfonamidopropyl)amine hydrochloride, 40 mL of CH$_2$Cl$_2$, 15 mL of a solution of 1 N aq. NaOH and 15 mL of saturated aq. NaCl were combined. After stirring vigorously for 30 min, the layers were separated and the organic portion dried (MgSO$_4$). Removal of the drying agent by filtration, concentration of the filtrate by rotary evaporation and further drying under vacuum (0.4 mm, 45° C.) for 24 h afforded 5.96 g (98%) of N-benzylbis(3-benzenesulfonamidopropyl)amine as a thick colorless oil. TLC (silica) : $R_f$=0.21, 1:1 (v/v) ethyl acetate:hexane. $^1$H NMR (CDCl$_3$/TMS) δ7.82 (d, 4 H, J=7 Hz, $SO_2ArH^{2,6}$), 7.51 (m, 6 H, $SO_2ArH^{3,4,5}$), 7.22 (m, 3 H, BnArH$^{2,4,6}$), 7.16 (m, 2 H, BnArH$^{3,5}$), 5.9 (br, 2 H, SO$_2$NH) 3.40 (s, 2 H, PhCH$_2$N), 2.92 (t, 4 H, SO$_2$NCH$_2$CH$_2$), 2.38 (t, 4 H, BnCH$_2$CH$_2$), 1.62 (quint, 4 H, NCH$_2$CH$_2$CH$_2$N) $^{13}$C NMR (CDCl$_3$) δ139.9, 138.2, 132.4, 129.0, 128.4, 127.2, 126.9, 58.7, 51.8, 42.2, 26.1. IR (NaCl plate, cm$^{-1}$) 3277 (br), 3061 (w), 1446 (s), 1325 (s), 1160 (s), 1093 (s).

b. 9-Benzyl-3-methylene-1,5-dibenzenesulfonyl-1,5,9-triazacyclododecane (compound 211).

In a 500 mL three-necked round-bottomed flask equipped with a rubber septum and a gas inlet, 0.92 g of a 60% (w/w) dispersion of sodium hydride in mineral oil (0.55 g NaH, 23 mmol) was washed with hexane (3×15 mL) under N$_2$. A solution of 5.78 g (11.5 mmol) of N-benzylbis(3-benzenesulfonamidopropyl)amine in 220 mL of DMF was added slowly with stirring. The resulting clear solution was stirred under N$_2$ while a solution of 1.44 g (11.5 mmol) of 3-chloro-2-chloromethyl-1-propene in 8 mL of DMF was added dropwise over 10 h. Stirring at room temperature under N$_2$ was continued for an additional 24 h. The solvent was removed by rotary evaporation evaporation using a hot water bath. A solution of the residue in 50 mL of CHCl$_3$ was washed with water (3×30 mL) and saturated aq. NaCl (2×30 mL) then dried (MgSO$_4$). Removal of the drying agent by filtration and concentration of the filtrate by rotary evaporation gave the crude product as a thick yellow oil. The oil was dissolved in 100 mL of 1:1 (v/v) ethyl acetate/hexane and filtered through a pad of 16 g of basic alumina (Act 1, 80–200 mesh) washing with an additional 50 mL of 1:1 ethyl acetate/hexane. Concentration of the combined filtrates under vacuum afforded 4.93 g (77 %) of 9-benzyl-3-methylene-1,5-dibenzenesulfonyl-1,5,9-triazacyclododecane as a bubbly film that was converted to the hydrochloride salt.

HCl Salt. A solution of the crude product in 30 mL of CHCl$_3$ was stirred for 30 m with 10 mL of 2 N aq. HCl and 10 mL of a saturated aq. NaCl solution. The organic layer was separated, washed with 20 mL of saturated aq. NaCl and concentrated by rotary evaporation. The residue was recrystallized by bringing an ethanol solution to a boil and adding ethyl acetate slowly until cloudiness occurs. After cooling to room temperature, the mixture was cooled to −25° C. for a period of 8 h giving a white solid that was isolated by vacuum filtration and recrystallized in a similar manner from acetone/ethyl acetate yielding 3.03 g (45%) of pure compound 211 (hplc), mp 135–136° C. A sample submitted for elemental analysis was dried for 24 h at 78° C. (0.3 mm). $^1$H NMR (DMSO-$d_6$) δ11.6 (br, 1 H, BnNH), 7.79 (d, J=7.8 Hz, 4 H, SO$_2$ArH$^{2,6}$), 7.68 (m, 8 H, SO$_2$ArH$^{3,4,5}$ BnH$^{3,5}$), 7.43 (m, 3 H, BnH$^{2,4,6}$), 5.37 (s, 2 H, C=CH$_2$), 4.30 (d, 2 H, PhCH$_2$N), 3.69 (s, 4 H, allylic), 3.09 (m, 8 H, SO$_2$NCH$_2$CH$_2$CH$_2$NBn), 1.95 (m, 4 H, NCH$_2$CH$_2$CH$_2$N). $^{13}$C NMR (CDCl$_3$) δ141.5, 136.9, 133.4, 131.1, 130.4, 129.7, 129.4, 128.8, 127.3, 118.8, 57.1, 51.8, 48.2, 46.3, 20.2. IR (KBr, cm$^{-1}$) 3060 (w), 2928 (w), 2873 (w), 2445 (br), 1447 (s), 1335 (s), 1163 (s), 1090 (m), 931 (m), 737 (s), 696 (m). UV (CH$_3$OH): $\lambda_{max}$ (loge), 224 (4.2). FABMS: m/z 554 (M+H$^+$, 100). Anal. calc. for $C_{29}H_{35}N_3S_2O_4$ HCl: C, 59.02; H, 6.15; N, 7.12; S, 10.86; Cl, 6.01. Found: C, 59.39; H, 6.28; N, 7.21; S, 11.34%

I.C. Synthesis of Compounds 214, 003 and 004

The synthesis of: 214 N-Benzyl-N-[3-(N-2-methyl-2-propenyl-toluenesulfonamido)propyl]-N-(3- toluenesulfonamidopropyl)amine dihydrogen sulfate 003 N-Benzylbis[3-(N'-2-methyl-2-propenyltoluenesulfonamido)propyl]amine dihydrogen sulfate 004 N-Benzylbis[3-(N'-2-propenyltoluenesulfonamido)propyl]amine dihydrogen sulfate is shown below:

δ142.95, 139.36, 136.94, 133.27, 129.52, 128.65, 128.01, 127.00, 126.72, 118.43, 58.3, 51.03, 50.70, 45.82, 25.98, 21.34. FT-IR (NaCl plate, cm$^{-1}$): 3064, 3027, 2924, 2802, 1920, 1643, 1598, 1494, 1453, 1418, 1337, 1159, 1091, 1020, 928, 815, 736, 700, 660.

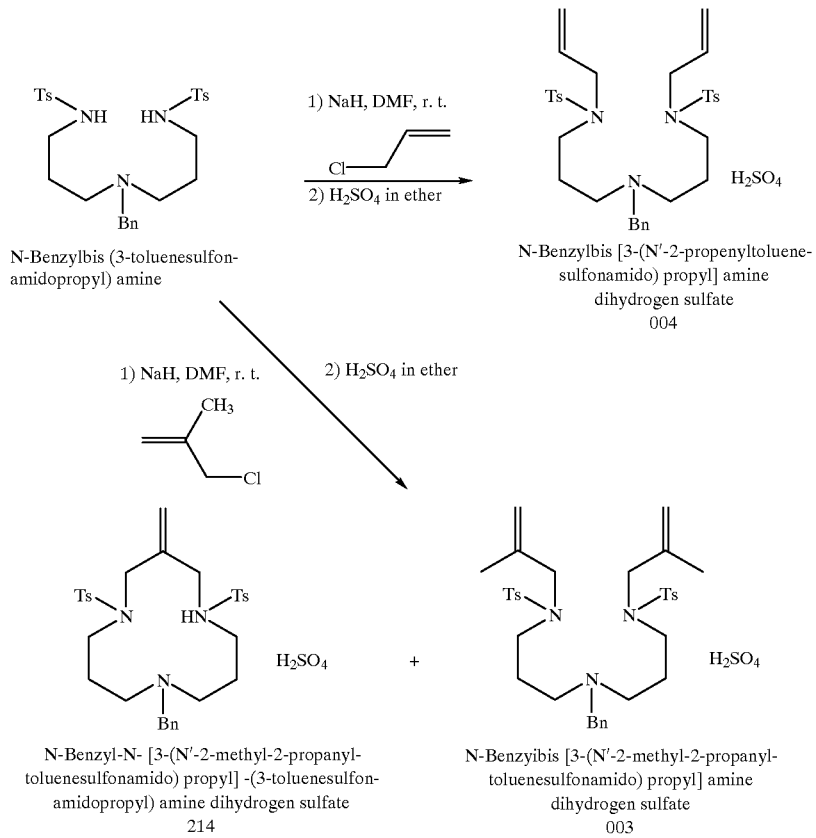

a. N-Benzylbis[3-N'-2-propenyltoluenesulfonamido)propyl]amine dihydrogen sulfate (Compound 004)

In a 250 mL three-necked round bottom flask equipped with rubber septum, a thermometer, a condenser and a nitrogen inlet, a solution of 432 mg (0.79 mmol) of N-benzylbis(3-toluenesulfonamidopropyl)amine (compound 2) in 25 mL anhydrous DMF was added to 125 mg of 60% (w/w) of sodium hydride in mineral oil (75 mg NaH, 1.88 mmol) that was previously washed with hexane (3×15 mL). The mixture was stirred for an hour at room temperature while a solution of 0.30 mL (3.68 mmol) of 3-chloropropene in 4.0 mL of anhydrous DMF was added dropwise. Upon completion of addition, stirring at room temperature under N$_2$ was continued for an additional 19 h. Vacuum filtration of the reaction mixture and concentration of the filtrate in vacuo gave 0.5 g (100%) of the crude product as a yellow oil. Free base: Preparative TLC of 202 mg of the crude product using 40% EtOAc in hexane on silica gel GF plates (1000 μm) yeilded 166 mg (82%) of the free base as a viscous, colorless oil. $^1$H-NMR (CDCl$_3$) δ7.66 (d, J=8.1 Hz, 4H, TsH$^{2,6}$), 7.27 (d, 4H, TsH$^{3,5}$), 7.24 (m, 5H, PhH), 5.61 (ddt, 2H, HC═CH$_2$), 5.11 (ddd, 4H, CH$_2$C═CHCH$_2$), 3.76 (d, J=6.3 Hz, 2H, NCH$_2$CH═CH$_2$), 3.44 (s, 2H, PhCH$_2$), 3.09 (dd, 4H, TsNCH$_2$CH), 2.40 (s, 6H, NSO$_2$PhCH$_3$), 2.35 (t, J=6.9 Hz, 4H, BnNCH$_2$) 1.66 (quintet, J=7.2 Hz, 4H, NCH$_2$CH$_2$CH$_2$). $^{13}$C-NMR (CDCl Compound 004: The purified free base (84 mg, 0.138 mmol) was dissolved in ether and stirred vigorously at 0° C. as a cold solution of 0.43 M H$_2$SO$_4$ in ether (0.32 mL) was carefully added dropwise. The white solid that precipitated was isolated by vacuum-filtration, washed with cold ether and dried in vacuo to give 94 mg (96%) of Compound 004. $^1$H-NMR (CDCl$_3$) δ7.66 (d, J=8.1 Hz, 4H, TsH$^{2,6}$), 7.27–7.42, (m, 5H, PhH), 7.30 (d, 8.1Hz, 4H, TsH$^{3,6}$), 5.50 (ddd, 2H, HC═CH$_2$), 5.19 (dd, J=16.8 Hz, 2H, trans-HC═CH$_2$), 5.16 (dd, J=9.9 Hz, 2H, cis HC═CH$_2$), 4.32 (s, 2H, PhCH$_2$) 3.72 (d, J=6.6 Hz, 4H, NCH$_2$CH═CH$_2$), 3.13 (m, 8H, BnCH$_2$CH$_2$), 2.41 (s, 4H, TsNCH$_2$CH$_2$), 2.16 (s, 4H, NCH$_2$CH$_2$CH$_2$). UV (MeOH) :s(λ$_{max}$) 24,000 (232). FABMS: m/z 610 (MH$^{30}$, 100).

b. N-Benzylbis [3-N'-2-methyl-2-propenyltoluenesulfonamido)propyl)amine dihydrogen sulfate (Compound 003) and N-Benzyl-N-[3-(N-2-methyl-2-propenyltoluenesulfonamido)propyl]-N-(3-toluenesulfonamidopropyl)]amine dihydrogen sulfate (Compound 214)

A solution prepared from 50 mL of anhydrous DMF, 1.14 g (2.15 mmol) of N-benzylbis(3-toluenesulfonamidopropyl)amine and 92 mg of 60% (w/w) sodium hydride in mineral oil (55 mg NaH, 2.30 mmol), which was previously washed with hexane (2×10 mL), was added over 2 h to a cold (0° C.) solution of 290 mg (3.23 mmol) of 3-chloro-2-methylpropene in 20 mL anhydrous DMF. The reaction mixture was stirred at room temperature under $N_2$ for 22 h, then vacuum-filtered. The filtrate was concentrated in vacuo to give 1.49 of product mixture which was dissolved in $CH_2Cl_2$ and separated by flash column chromatography using 230–400 mesh silica gel (Merck) and 45–50% EtOAc in hexane. The collected fractions were analyzed by TLC using 50% EtOAc in hexane. Compound 003 free base eluted first and was obtained as a colorless oil, 234 mg (19%). $^1$H-NMR (CDCl$_3$) δ7.65 (d, J=8.1 Hz, 4H, TsH$^{2,6}$), 7.26 (d, J=7.8 Hz, 4H, TsH$^{3,5}$), 7.22 (m, 5H, PhH), 4.84 (d, J=5.1 Hz, 4H, CH$_2$=CHCH$_2$), 3.63 (s, 4H, NCH$_2$CH=CH$_2$), 3.38 (s, 2H, PhCH$_2$), 3.04 (dd, J=7.8 Hz, 4H, TsNCH$_2$CH$_2$) 2.40 (s, 6H, NSO$_2$PhCH$_3$), 2.26 (t, J=6.6 Hz, 4H, BnNCH$_2$), 1.70 (s, 3H, CH$_3$—CH=CH$_2$), 1.60 (quintet, J=7.8 Hz, 4H, NCH$_2$CH$_2$CH$_2$). $^{13}$C-NMR (CDCl$_3$) δ142.97, 140.94, 139.98, 136.98, 129.54, 128.70, 128.07, 127.10, 126.78, 114.22, 58.14, 54.77, 51.14, 46.50, 25.79, 21.40, 19.75. FT-IR (NaCl plate, cm$^{-1}$): 3028, 2944, 1813, 1658, 1598, 1494, 1454, 1336, 1160, 1005, 918, 817, 699, 655. Anal. calc. for $C_{33}H_{47}N_3O_4S_2$: C, 65.90; H, 7.43; N, 6.59; S, 10.05%. Found: C, 65.81; H, 7.31; N, 6.59; S, 10.14%. Compound 214 free base eluted next and was obtained as a colorless oil, 422 mg (35%). $^1$H-NMR (CDCl$_3$) δ7.67 (d, J=8.3 Hz, 4H, TsH$^{2,6}$), 7.25 (m, 9H, PhH, TsH), 6.10 (br s, 1 H, TsNH), 4.87 (s, 2H, CH$_2$=CMeCH$_2$), 3.64 (s, 4H, NCH$_2$CH=CH$_2$), 3.42 (s, 2H, PhCH$_2$), 3.06 (dd, 2H, TsRNCH$_2$CH$_2$), 2.94 (br dd, 2H, NHTsCH$_2$), 2.42 (s, 6H, NSO$_2$PhCH$_3$), 2.39 (t, 2H, BnNCH$_2$CH$_2$CH$_2$NRTs), 2.33 (t, 2H, (BnNCH$_2$CH$_2$CH$_2$NHTs), 1.69 (s, 3H, CH$_3$—CH=CH$_2$), 1.69 (quintet, 2H, TsRNCH$_2$CH$_2$CH$_2$), 1.58 (quintet, 2H, TsHNCH$_2$CH$_2$CH$_2$). $^{13}$C-NMR (CDCl$_3$) δ143.15, 141.00, 138.61, 129.66, 129.56, 128.98, 128.43, 127.22, 127.07, 114.47, 58.68, 54.96, 52.55, 51.25, 46.61, 42.79, 25.76, 21.44, 19.18.

Compound 214: A solution of the purified free base (366 mg, 0.627 mmol) in 40 mL of ether was stirred vigorously at 0° C. as a cold solution of 0.18 M H$_2$SO$_4$ in ether (2.0 ml,) was carefully added dropwise. The white solid that precipitated was isolated by vacuum-filtration, washed with cold ether and dried in vacuo to give 410 mg (96i) of Compound 214. $^1$H-NMR (CDCl$_3$ δ7.76 (d, J=8.4 Hz, 2H, TsH$^{2,6}$), 7.65 (d, J=8.4 Hz, 2H, TsH$^{2,6}$), 7.39–7.48 (m, 5H, PhH), 7.28(d, J=8.3 Hz, 2H, TsH$^{3,5}$), 7.24 (d, J=7.8 Hz, 2H, TsH$^{3,5}$), 6.49 (br s, 2H, TsNH, HSO$_4$), 4.80 (dd, 2H, CH$_2$=CMeCH$_2$), 4.28 (dd, 2H, TsRNCH$_2$CH$_2$), 3.52 (dd, 2H, PhCH$_2$), 3.21 (br dd, 2H, TsHNCH$_2$CH$_2$), 3.01 (br dt, 6H, NCH$_2$CH=CH$_2$), 2.39 (t, 3H, NSO$_2$PhCH$_3$), 2.34 (s, 3H, NSO$_2$PhCH$_3$), 2.08 (quintet, 4H, NCH$_2$CH$_2$CH$_2$N), 1.54 (s, 3H, CH$_3$—CH=CH$_2$). $^{13}$C-NMR (CDCl$_3$) δ143.57, 142.97, 140.06, 137.12, 135.79, 131.42, 130.03, 129.81, 129.68, 129.39, 128.11, 127.332, 127.15, 115.56, 57.042, 55.55, 51.122, 49.96, 45.80, 40.16, 24.08, 23.24, 21.41, 21.38, 19.79. UV (MeOH) :s( max) 24,000 (232).

c. Compound 003

A solution of the purified free base (210 mg, 0.329 mmol) in 15 mL of ether was stirred vigorously at 0° C. as a cold solution 0.43 M H$_2$SO$_4$ in ether (0.76 mL) was carefully added dropwise. The white solid that precipitated was isolated by vacuum-filtration, washed with cold ether and dried in vacuo to give 238 mg (98%) of Compound 003. $^1$H-NMR (CDCl$_3$) δ7.68 (d, J=7.8 Hz, 4H, TsH$^{2,6}$), 7.53 (br d, J=4.2 Hz, 2H, PhH), 7.43 (d, J=3.3 Hz, 3H, PhH), 7.30 (d, J=7.8 Hz, 4H, TsH$^{3,5}$), 4.86 (d, J=4.2 Hz, 4H), 4.28 (s, 2H, PhCH$_2$), 3.58 (s, 4H, NCH$_2$CH=CH$_2$), 3.09 (m, 8H, TsNCH$_2$CH$_2$), 2.40 (s, 6H, NSO$_2$PhCH$_3$), 2.13 (quintet, 4H, NCH$_2$CH$_2$CH$_2$), 1.61 (s, 3H, CH$_3$—CH=CH$_2$). $^{13}$C-NMR (CDCl$_3$) δ142.97, 140.94, 139.98, 136.98, 129.54, 128.70, 128.07, 127.10, 126.78, 114.22, 58.14, 54.77, 51.14, 46.50, 25.79, 21.40, 19.75. UV (MeOH):s ($λ_{max}$) 23,000 (232), Anal. calc. for $C_{35}H_{47}N_3O_4S_2 \cdot H_2SO_4$: C, 57.12; H, 6.71; N, 5.71; S, 13.07%. Found: C, 57.97; H, 6.90; N, 5.77; S, 12.45%. FABMS: m/z 638 (MH$^+$, 100).

II. Synthesis of Compounds 12, 13, 14, 15, 16, 17

The synthesis of 12 3-Methylene-1,5-ditosyl-1,5,9-triazacyclododecane, 13 5,9-Ditosyl-7-hydroxymethyl-1,5,9-triazabicyclo-[5,5,0] tridecane, 14 5,9-Ditosyl-13-oxa-1,5,9-triazatricyclo[5,5,1$^{1,7}$,1$^{7,12}$] -tetradecane, 15 9-Benzyl-3-hydroxymethyl-1,5-ditosyl-1,5,9-triazacyclododecane, 16 9-Benzyl-3-chloromethyl-1,5-ditosyl-1,5,9-triazacyclododecane, and 17 3-Chloromethyl-1,5-ditosyl-1,5,9-triazacyclododecane is shown in Scheme 2.

SCHEME 2

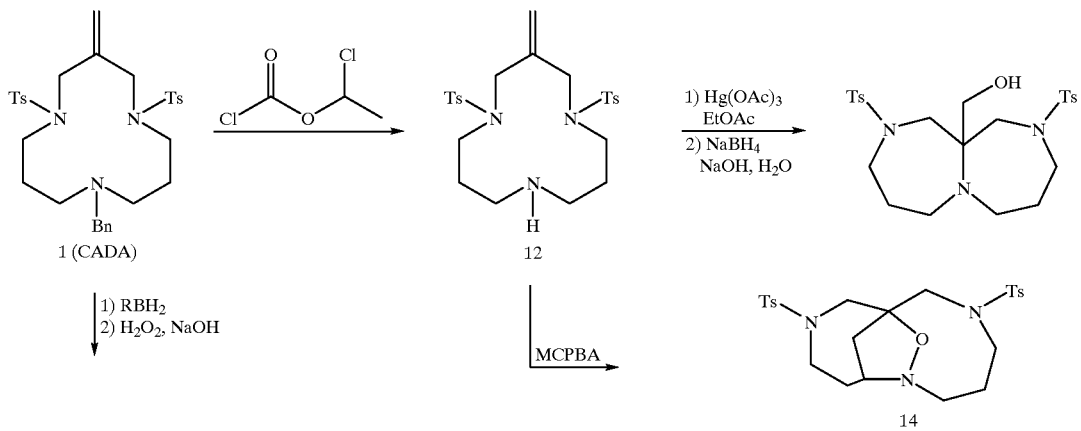

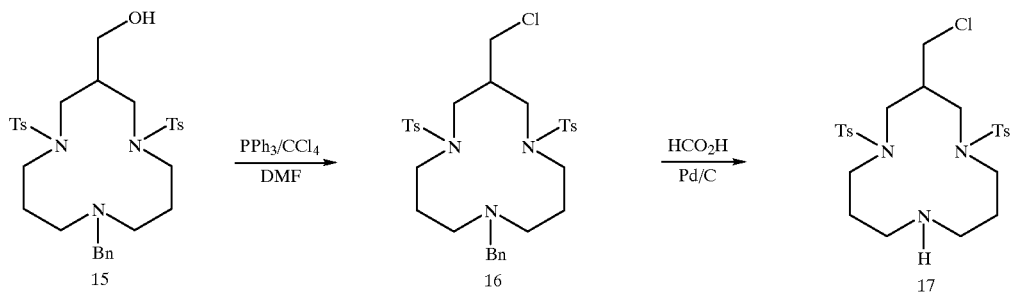

a. The benzyl group of Compound 1 (CADA) was removed by reaction with alpha-chloroethyl chloroformate (ACE-Cl) giving the secondary amine (compound 12).

b. Intramolecular aminomercuration of 12 by reaction with mercuric acetate followed by alkaline reduction gave bicyclic alcohol 13 (53%) after separation of the product mixture by chromatography.

c. Oxidation of 12 with m-chloroperoxybenzozc acid gave isoxazolidine 14 (20%), apparently via the nitrone produced by oxidation at nitrogen prior to epoxidation of the exocyclic double bond.

d. Functionalization of the alkene moiety was carried out via hydroboration of 1 with thexylborane, yielding alcohol 15 after alkaline hydrogen peroxide workup.

e. Chloro analogue 16 was then prepared by reaction of 15 with triphenylphosphine and CCl$_4$, and debenzylation to 17 was performed by reaction of 16 with formic acid and 5% palladium-on-carbon.

III. Synthesis of Compounds 18, 19, 21, 22, 23, 24, and 26

The synthesis of

18 N,N-bis(3-toluenesulfonamidopropyl)toluenesulfonamide,
19 1,5,9-Tritosyl-1,5,9-triazacyclododecane,
21 11-Methylene-1,5,9-triazabicyclo[7,3,3]pentadecane,
22 3-Methylene-1,5,9-tritosyl-1,5,9-triazacyclododecane,
23 3-Hydroxymethyl-1,5,9-tritosyl-1,5,9-triazacyclododecane,
24 3-Chloromethyl-1,5,9-tritosyl-1,5,9-triazacyclododecane,
26 1,5,9-Triazabicyclo[9,1,1]tridecane is shown in Scheme 3.

SCHEME 3

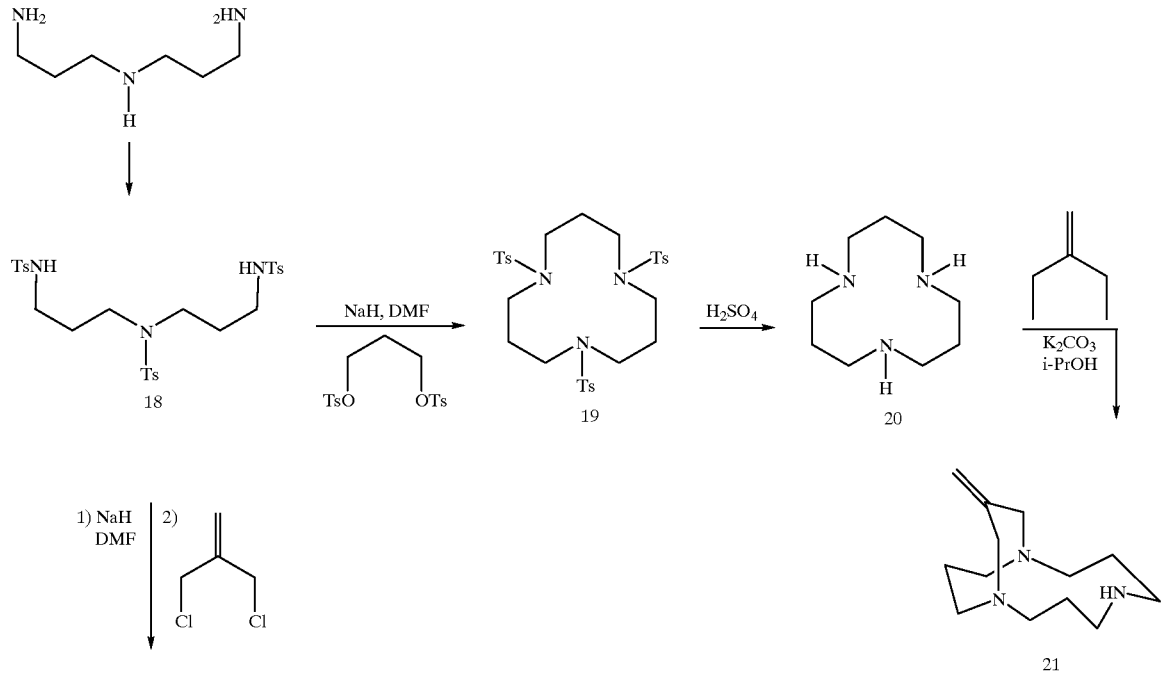

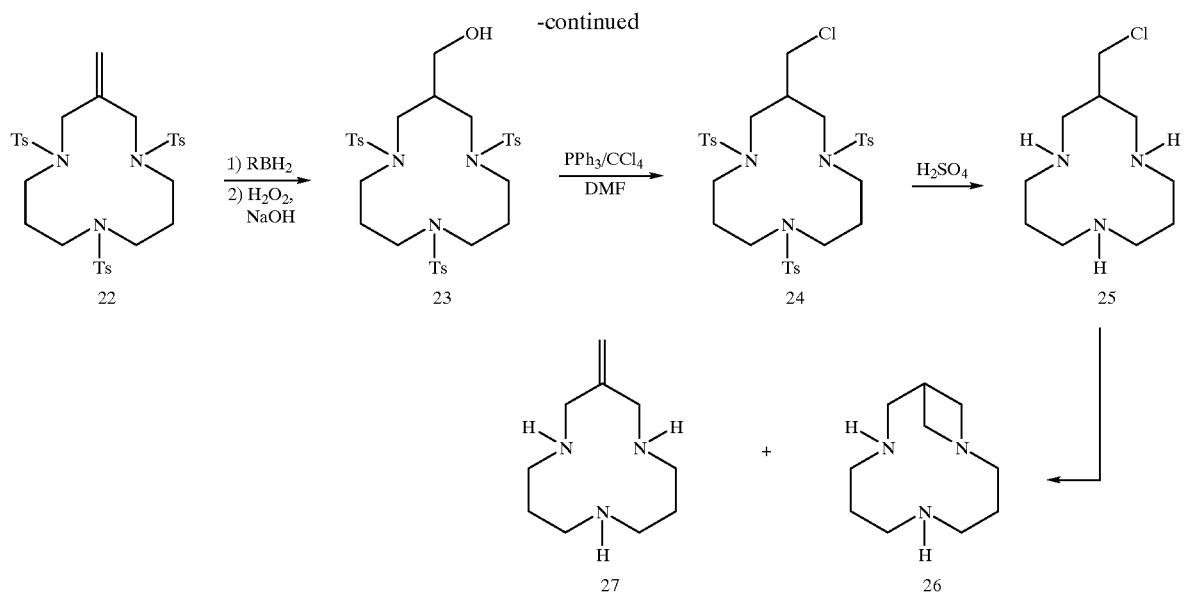

a. The tritosylamide amide (compound 18) is prepared by tosylation of N,N-bis(3-aminopropyl)amine (commercially available)

b. Cyclization of the disodium salt of 18 with propylene glycol ditosylate gave macrocycle 19 (50%).

c. Macrocycle 19 was detosylated to 1,5,9-triazacyclododecane 20 (60%) by treatment with 98% sulfuric acid at 100° C.

d. Macrocyclic triamine 20 is commercially available, but is readily prepared in multiple-gram quantities and the yield of 19 has been improved to 70%.

e. Reaction of 20 with 3-iodo-2-iodomethyl-1-propene gave bicyclic analogue 21 in 60–70% yield.

f. Alkene 22(59%) was prepared by Richman-Atkins cyclization of 18 with 3-chloro-2-chloromethyl-1-propene.

g. Another series of analogues was prepared from alkene 22.

By methods described previously for functionalization of compound 2 (Scheme 1), hydroboration/oxidation of 22 gave alcohol 23, which was then converted to chloride 24 in greater than 90% yield overall. The chloromethyl group of 25 survives the harsh conditions required for tosyl cleavage, yielding 25. Transannular cyclization was attempted by treating this compound with potassium carbonate in isopropanol, but a 59% yield of azetidine 26 was obtained along with a minor amount of elimination product (27).

All of the analogues appearing in Schemes 1–3 can be synthesized in multiple-gram quantities by these methods. Most can be purified by recrystallization. Certain amines in these series occur as viscous oils or glasses, but in many cases crystalline HCl salts can be obtained. The HCl salts of 1 and 2 have also been prepared, with the expectation that enhanced water solubility improves the ease of administration of these drugs.

IV. Synthesis of Compounds 41, 42, 43, 44, 45 and 46

Other symmetrical analogues 41 9-Benzyl-3-keto-1,5-ditosyl-1,5,9-triazacyclododecane
42 9-Benzyl-3-methyl-1,5-ditosyl-1,5,9-triazacyclododecane
43 9-Benzyl-3-methylene-1,5-ditosyl-1,5,9-triazacyclododecane-9-oxide
44 9-Acyl-3-methylene-1,5-ditosyl-1,5,9-triazacyclododecane
45 9-Alkyl-3-methylene-1,5-ditosyl-1,5,9-triazacyclododecane
46 9-Acyl-3-methylene-1,5-ditosyl-1,5,9-triazacyclododecane epoxide in the family of triaza compounds to be used in the invention are shown in Scheme 4.

SCHEME 4

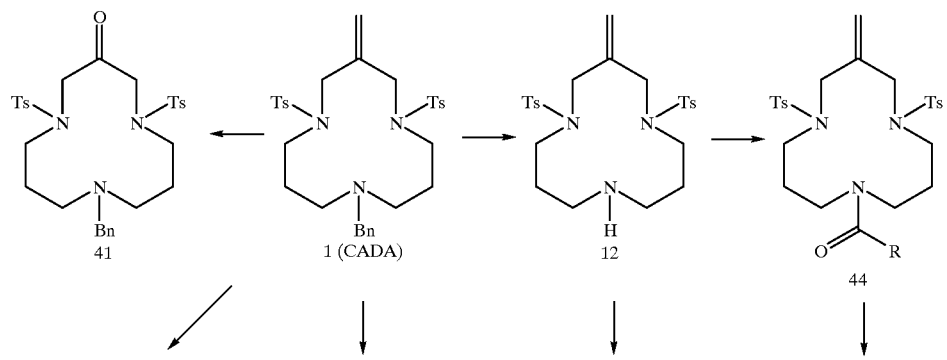

-continued

42

43

45

46

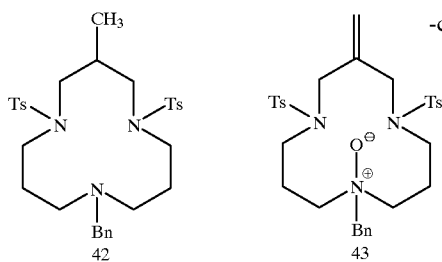 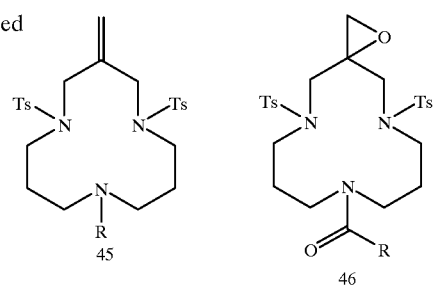
Compounds 41 to 46 are closely related to CADA. They are designed to have enhanced water solubility and to be capable of modification of biomolecules by electrostatic or hydrophobic interaction at the double bond position for reversible binding of proteins, such as HIV capsid proteins, integrase or proviral DNA by $SN^2$ attack of an O, N or S at W.

Compounds 41, 42 and 43 are prepared in one step by oxidation or reduction of 1. Ketone 41 is prepared by ozonolysis of 1-HCl in methanol, followed by reductive workup with dimethyl sulfide. The exocyclic double bond is reduced to give 42 by catalytic hydrogenation under conditions known for hydrogenation of disubstituted alkenes in the presence of benzylamine Functionality.

Compound 41 has improved water solubility and 42 has similar polarity to 1, but neither can undergo the $S_N2'$ covalent binding mechanism mentioned above.

Ketone 41 is capable of Schiff-base condensation with an amino group (e.g. of a lysine side-chain). Amine N-oxide 43 is prepared by reaction of 1 with hydrogen peroxide in methanol. The water solubility of this compound should be similar to that of 1•HCl so it can be used to test whether the protonation equilibrium (1=1•$CH^+$) is important to the mechanism of action. Compound 12, previously prepared according to Scheme 2, is an important analogue of 1 and an intermediate in the synthesis of 44–46. Acylation to 44 (R═H, alkyl or aryl) replaces the benzyl group with acyl groups of various sizes to test the steric and electronic requirements for this site. If protonation of the nitrogen atom is important, then alkylation of 12 to 45 (R=methyl, ethyl, β-hydroxyethyl, isopropyl, etc.) independently tests the effects of steric bulk and polarity at this site. A series of analogues of type 45 can be prepared in which R is a benzyl group bearing a polar substituent (OH, $NO_2$, $SO_3H$, $CO_2H$, $NH_2$ or $NMe_2$) to solubilize the drug. Finally, epoxidation of 44 with m-CPBA or Oxone will give 46 with enhanced polarity and reactivity at the exocyclic site toward nucleophilic attack.

Synthesis of compound 43 was as follows:

43

9-Benzyl-3-methylene-1,5-ditosyl-1,5,9-triaza-9-N-oxide-cyclododecane (ARB 95-212) (Compound 43).

$H_2O_2$Method. In a 250 mL round-bottomed flask, 3.00 g (5.2 mmol) of CADA was diluted with 100 mL of ethanol and 30 g of 30% $H_2O_2$. A magnetic stir bar was added, condenser attached and the mixture was heated by means of an oil bath to reflux. After 5 h, the clear solution was allowed to cool and then concentrated by rotary evaporation. The residue was diluted with 50 mL of $CHCl_3$ and 30 mL of water and stirred briefly to dissolve the contents. The organic layer was separated, washed with water (2×25 mL) then with 25 mL of saturated aq. NaCl and dried ($MgSO_4$). Filtration of the drying agent and concentration of the filtrate afforded a bubbly film. Further purification was performed by gravity column chromatography with neutral alumina. (Act. 1, 60–325 mesh) using $CHCl_3$ followed by 20:1 (v/v) chloroform:ethanol to elute Compound 43. Concentration of the fractions to a bubbly film followed by trituration with acetone afforded 1.44 g (47i) of Compound 43 as a white solid, mp 129–130° C.

Oxone Method. A mixture of 2.50 g (4.29 mmol) of CADA, 1.25 g (14.8 mmol) of sodium hydrogen carbonate, 2.71 g (4.4 mmol) of Oxone, 25 mL of water and 75 mL of ethanol was stirred with a magnetic stir bar and heated (oil bath) to 45–50° C. for 24 h. After cooling to room temperature, the solid was removed by suction filtration and washed with 40 mL of ethanol (CADA was recovered by washing the solid with $CHCl_3$ and concentration of the chloroform filtrate). The combined ethanol filtrates were concentrated and a $CHCl_3$ solution of the residue was dried over $MgSO_4$. Removal of the drying agent by filtration and concentration of the filtrate afforded 1.20 g (46%) of Compound 43 ($^1H$ NMR) as a bubbly film. Purification by gravity column chromatography with neutral alumina as described in the previous method afforded 0.35 g of Compound 43 as a white solid after trituration with acetone. A sample submitted for elemental analysis was dried at 400C (0.2 mm) for 4 h. TLC (alumina) : $R_f$=0.36, 20:1 (v/v) chloroform:ethanol. $^1H$ NMR ($CDCl_3$/TMS) δ7.65 (m, 2 H, $BnArH^{3,5}$), 7.62 (d, J=8.1 Hz, 4 H, $TsH^{2,6}$), 7.40 (m, 3 H, $BnArH^{2,4,6}$), 7.32 (d, J=8.1 Hz, 4 H, $TsH^3$s), 5.33 (s, 2 H, C═$CH_2$), 4.29 (s, 2 H, $PhCH_2$), 3.70 (s, 4 H, allylic), 3.45 (t, 4 H, Bn-N(O)-$CH_2$), 3.10 (t, 4 H, Ts-$NCH_2$), 2.45 (s, 6 H, $TsCH_3$), 2.10 (m, 4 H, $NCH_2CH_2$). $^{13}C$ NMR ($CDCl_3$) δ144.0, 141.7, 133.7, 132.4, 130.0, 129.8, 129.3, 128.3, 127.5, 118.8, 71.9, 61.2, 52.7, 48.8, 22.0, 21.5. IR (KBr, $cm^{-1}$) 3063 (w), 3032 (w), 2951 (w), 2925 (w), 2867 (w), 1598 (w), 1458 (m), 1339 (s), 1162 (s), 1090 (m), 1034 (w). UV ($CH_3OH$): $\lambda_{max}$ (loge), 230 (4,4). FABMS: m/z 598 ($M+H^+$, 41). Anal. calc. for $C_{31}H_{39}N_3S_2O_5$: C,62.29; H, 6.58; N, 7.03; S, 10.73. Found: C, 61.92; H, 6,53; N, 7.24; S, 10.97%.

An analogue of compound 44 is compound 213 9-(Ethyloxycarbonyl)-3-methylene-1,5-ditosyl-1,5,9-triazacyclododecane.

21

Compound 213 was prepared as follows:

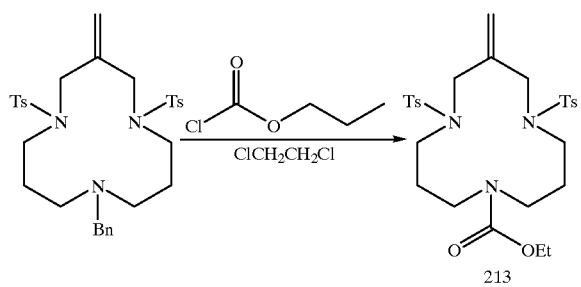

9-(Ethyloxycarbonyl)-3-methylene-1,5-ditosyl-1,5,9-triazacyclododecane (compound 213). In an oven dried 250 mL round-bottomed flask, 8.20 g (14.1 mmol) of CADA was diluted with 65 mL of freshly distilled ($P_2O_5$)1,2-dichloroethane. A magnetic stir bar, reflux condenser with a gas inlet and oil bath were added then the system purged with nitrogen. Ethyl chloroformate (1.70 mL; 17.8 mmol) was added by syringe and the solution heated at reflux for 5 h. The solvent was removed using a rotary evaporator with a 40° C. water bath. Dilution of the oily residue with 60 mL of a solution of 2:3 (v/v) ethyl acetate:hexane caused a white precipitate to form at room temperature after scratching the glass. The solid was filtered and washed with 3×30 mL of a solution of 2:3 (v/v) ethyl acetate:hexane giving 6.63 g (83%) of Compound 213, mp 125–126° C. (after drying at 78° C. and 0.9 mm for 19 h). TLC (silica): $R_f$=0.24, 1:1 (v/v) ethyl acetate:hexane. $^1$H NMR (CDCl$_3$/TMS) δ7.68 (d, J=8.3 Hz, 4 H, SO$_2$ArH$^{2,6}$), 7.33 (d,J=8.3 Hz, 4 H, SO$_2$ArH$^{3,5}$), 5.21 (s,2 H, C=CH$_2$), 4.07 (quart., J=7 Hz, 2 H, CO$_2$CH$_2$CH$_3$), 3.85 (s, 4 H, allylic), 3.33 (t, J=6.4 Hz, 4 H, EtO$_2$CNCH$_2$), 3.11 (m, 4 H, SO$_2$NCH$_2$), 2.44 (s, 6 H, PhCH$_3$), 1.85 (m, 4 H, NCH$_2$CH$_2$CH$_2$N), 1.21 (t, J=7 Hz, 3 H, CO$_2$CH$_2$CH$_3$). $^{13}$C NMR (CDCl$_3$) δ157.0, 143.6, 139.4, 135.7, 129.8, 127.2, 116.9, 61.2, 51.4, 45.5, 45.2, 28.0, 21.4, 14.7 IR (KBr, cm$^{-1}$) 2990 (w), 2990 (w), 2948 (w), 1688 (s), 1598 (w), 1485 (m), 1424 (m), 1343 (s), 1230 (s), 1154 (s), 1093 (s), 1027 (m), 903 (m), 818 (m), 788 (m). FABMS: m/z 564 (M+H$^+$, 100). Anal. calc. for C$_{27}$H$_{37}$N$_3$S$_2$O$_6$: C, 57.53; H, 6.62; N, 7.45; S, 11.37. Found: C, 57.36; H, 6.54; N, 7.73; S, 11.74%.

22

V. Synthesis of Compounds 50, 51, 52 and 53

Another series of compounds is illustrated by formula II. These compounds include 50  9-Benzyl-1-formyl-3-methylene-1,5,9-triazacyclododecane
51  9-Benzyl-1-formyl-3-methylene-5-tosyl-1,5,9-triazacyclododecane
52  9-Benzyl-3-methylene-1-tosyl-1,5,9-triazacyclododecane
53  e.g. 9-Benzyl-3-methylene-1-acyl-5-tosyl-1,5,9-triazacyclododecane formula II

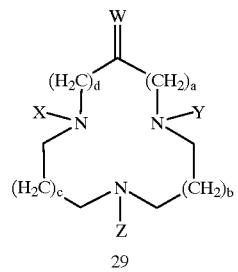

29

These compounds have three different substituents (X, Y and Z) on the three nitrogen atoms of a 12-membered ring. The synthetic plan utilizes a series of reactions reported for selective, unsymmetrical substitution of 1,5,9-triazacyclododecane. The intermediate is 3-methylene-1,5,9-triazacyclododecane (27), which can be obtained quantitatively by elimination of HCl from 25 Scheme 3. Reaction of 27 with neat DMF dimethyl acetal gives 47 in high yield as shown in Scheme 5. Monoalkylation with benzyl bromide will give 48 or 49 (or both). Both of these salts are synthetically useful, but the completion of the synthesis is illustrated with 48.

SCHEME 5

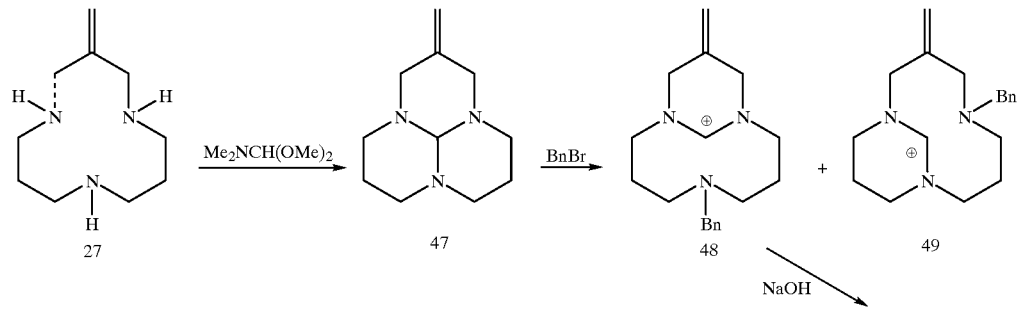

-continued

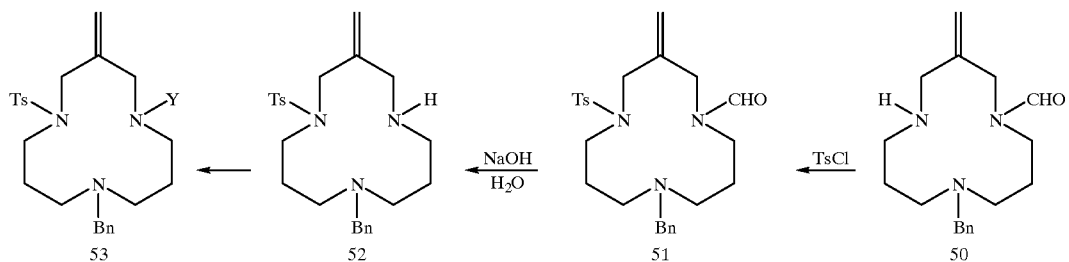

Alkaline hydrolysis will yield formamide 50, which is an unsymmetrical example of formula 29, where X=H, Y=CHO and Z=benzyl. Tosylation of 50 and alkaline hydrolysis will give 51 and 52 respectively. Compound 52 is a mono-detosylated analogue of 1 and the missing tosyl group can be replaced with almost any alkyl, acyl, alkanesulfonyl or arenesulfonyl group of interest (53, Y=various For example, Y=benzyl shows the effect of two protonation sites, while Y=p-bromobenzensulfonate shows the effect of enhancing the sulfonamide leaving group ability. Candidates for improved water solubility include compounds of type 29 in which Z=benzyl and X and Y are benzenesulfonyl groups bearing polar substituents, such as $NH_2$, OH or $CO_2H$.

VI. Synthesis of macrocyclic triamines of varying ring size: compounds 55 and 60

Varied ring size and incorporation of amide functionality into the lare ring in macrocylic lactams are shown in Scheme 6.

SCHEME 6

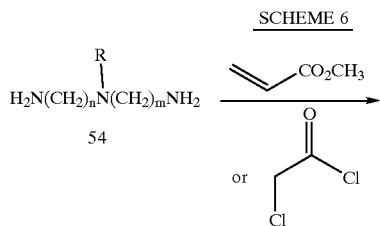

-continued

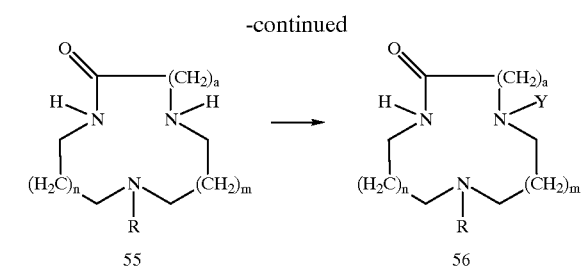

Almost any linear triamine of type 54 (m, n=2–6, R=alkyl, aryl or acyl) is available by methods used for the synthesis of linear and macrocyclic polyamines. Cyclization of these triamines with methyl acrylate or chloroacetyl chloride gives the corresponding macrocycles (55; a=2 or 1, respectively).

The acrylate cyclization is precedented by formation of the phenyl-substituted analogue of 55 (a=2, m=1, n=1, R=H) by reaction of the triamine with methyl cinnamate. Chloroacetyl chloride has been used in the syntheses of numerous polyazamacrocycles by the so-called crablike cyclization, which is usually carried out in refluxing acetonitrile without resort to high-dilution conditions. The low reactivity of the amide nitrogen atom of 55 enables selective functionalization of the third nitrogen, affording 56 (Y=alkyl, acyl, alkanesulfonyl or arenesulfonyl). Both series of macrocyclic lactams (55 and 56) can then be reduced to macrocyclic triamines under various conditions for the reduction of amides to amines. The resulting compounds are saturated analogues of type 29 bearing three different X, Y and Z groups, any of which could bear water-solubilizing substituents, and having ring sizes in the range of 9–18 carbon and nitrogen atoms.

VII. Synthesis of open-chain or non-macrocyclic analogues 58, 59, 60, 61, 61, 63 and 64

Open-chain and non-macrocyclic analogues are shown in Scheme 7.

SCHEME 7

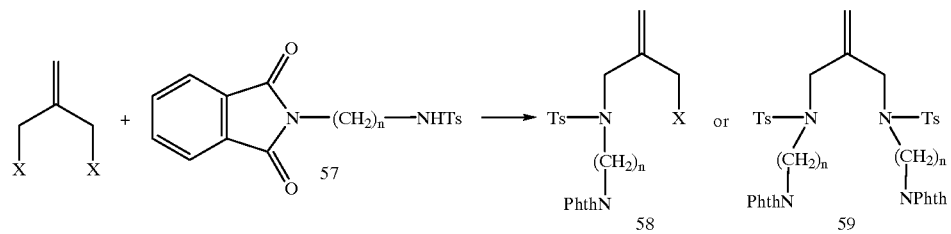

-continued

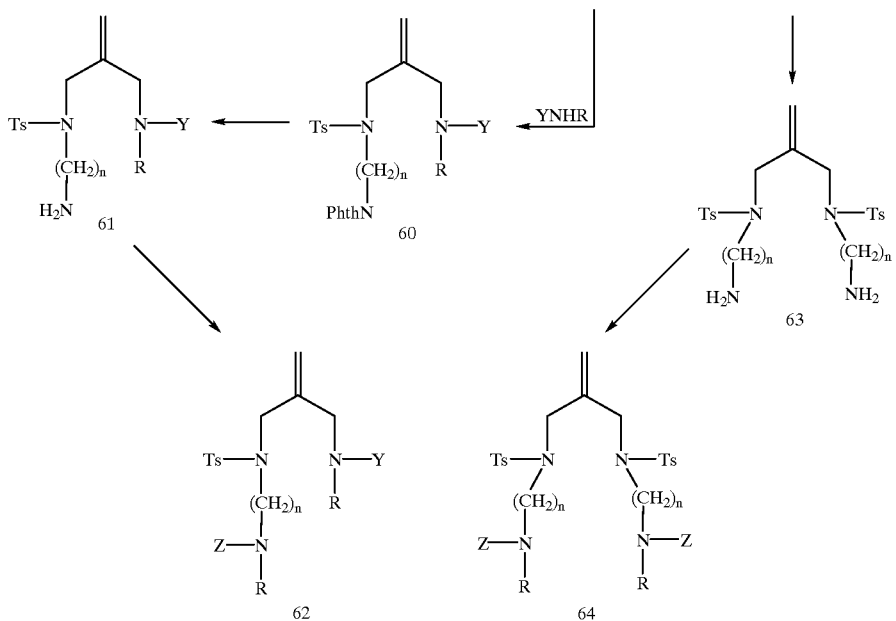

These analogues are synthesized from a series of 1,n-alkanediamines via the N-tosylphthalimide derivatives (57, n=2–7). Alkylation of the sodium, potassium or cesium salt of 57 with either 2-chloromethyl-3-chloro-1-propene or 2-iodomethyl-3-iodo-1-propene will give chain-extended intermediate 58 or 59. It is possible to control the product selectivity of the reaction by varying stoichiometry and order of addition of the reactants. Intermediates of type 58 bear a second leaving group (X), which will be displaced by various amine or sulfonamide nucleophiles, yielding 60 (Y=R',$SO_2$R' or $SO_2$Ar). Cleavage of the phthalimide protecting group by hydrazine will give primary amine 61, which can be acylated or sulfonated to analogue series 62. The same Gabriel synthesis approach can be applied to 59 (n=2–8); an unsymmetrical series of compounds, differing only chain length relative to 59, can be prepared by reaction of 58 with 57. The resulting series of compounds includes symmetrical and unsymmetrical open-chain analogues of 1 containing the allylic tosylamide functionality and a total of 3–4 nitrogen atoms.

VIII. Synthesis of bicyclic compounds 66, 67 and 68

An additional series of analogues consists of the bicyclic compounds 34–36 shown below:

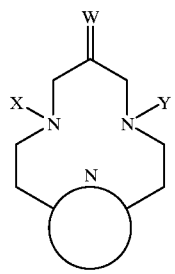

34

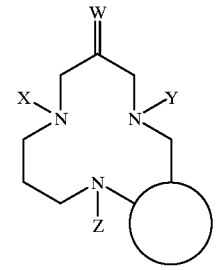

35

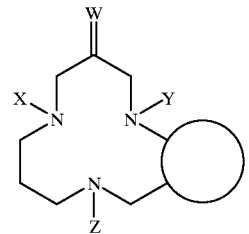

36

Examples of these bicyclic compounds and their syntheses are shown in Scheme 8.

SCHEME 8

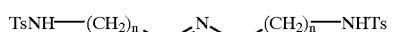
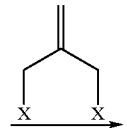

65

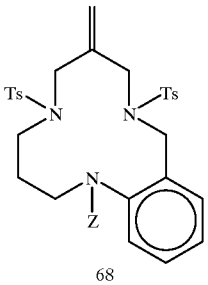

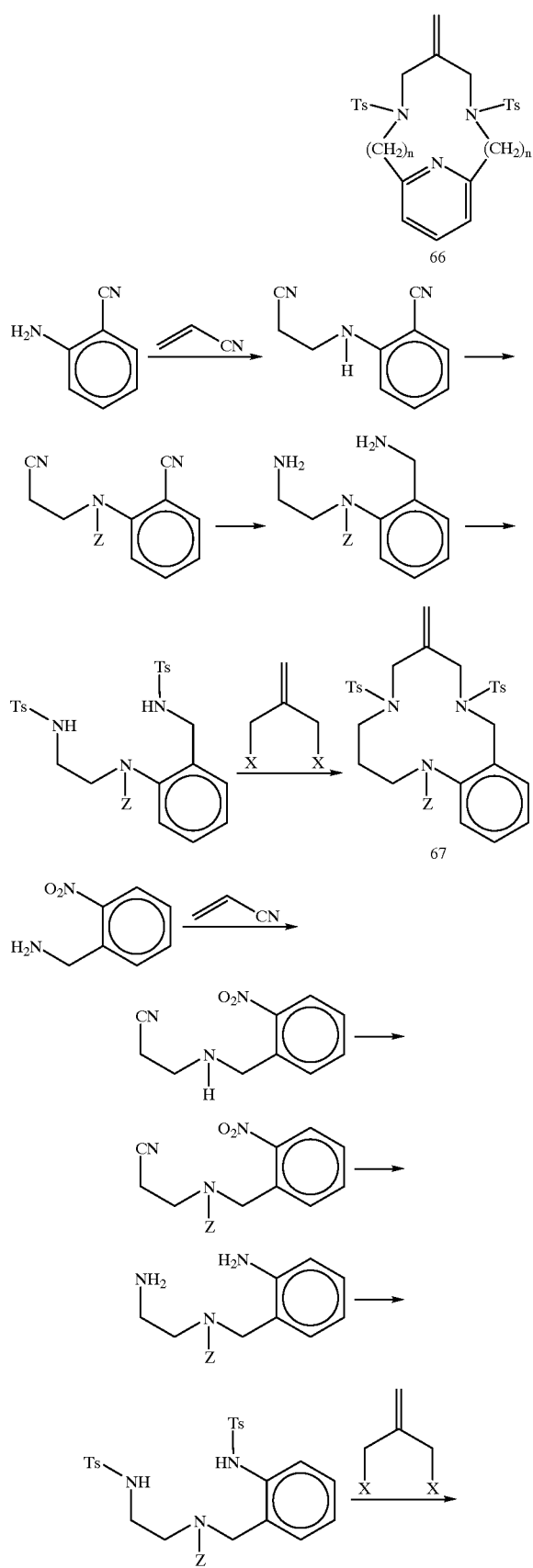

In bridged pyridine compound 66, corresponding to 34, the tertiary amino basic site is replaced by a pyridine nitrogen atom and the aromatic benzyl group is replaced by the aromatic pyridine ring. The Richman-Atkins synthetic approach shown has been used successfully in the preparation of many bridged pyridine host compounds. By analogy with known cyclizations of 65 (n=1), reaction with 2-chloromethyl-3-chloropropene or 2-iodomethyl-3-iodopropene under high-dilution conditions gives analogue 66 (n=1). The entire series in which n=1–6 is preparable by this method. In 35 and 36 the second ring is fused to two carbon atoms of CADA, leaving the center nitrogen atom free for substituent Z. Two benzene fused examples of 35 and 36 are 67 and 68, which are shown in Scheme 8 with their syntheses. The five steps shown in each case parallel the 5-step synthesis of CADA (Scheme 1) and yields should be comparable. The fused benzene ring mimics the benzyl group of CADA, leaving substituent Z variable. In all three cases (66–68) the fused aromatic ring can bear polar substituents enhancing water solubility.

Other analogs such as those functionalized with polar groups for increased solubility can be synthesized using the synthesis methods described above, coupled with various steps known in the art and described, e.g., by T. J. Richman et al., Macrocyclic Polyamines: 1,4,7,10,13,16-Hexaazacyclooctadecane in *Organic Synthesis, Coll. Vol. VI,* Noland, W. E., Ed., Wiley, New York, 1988, pp. 652–662; Bradshaw et al. *Aza-Crown Macrocycles,* Wiley, New York, 1993, chpt. IV.

Such polar groups include, for example, NO, $NO_2$, $NH_2$, OH, SH, OR, SR, COR, $SO_2R$, SOR, halide (F, Cl, Br, I) NHR, $NR_2$, HCO, COOH, COOR, C≡N, alkyl halide, etc. (R=alkyl of 1–10 carbons).

Antiviral activity was tested as follows:

EXAMPLE 1

In these tests, the $IC_{50}$ (50% inhibitory concentration) is the concentration resulting in 50% cellular toxicity. $EC_{50}$ (median effective concentration) is the compound concentration that reduces infection by 50%. The effectiveness of a compound against a virus is expressed as $TI_{50}$ (median therapeutic index) which is determined by the ratio $IC_{50}/EC_{50}$.

Compounds of the invention were tested to assess the efficacy of the inhibitory effect of the compounds against HIV. The screen was carried out in a soluble formazan assay by the tetrazolium method according to Weislow et al., J. Natl. Cancer Inst. 81:577–586, 1989.

The compound was dissolved in dimethyl sulfoxide (DMSO) (final conc. less than 0.25%) and then diluted 1:100 in cell culture medium. Because DMSO is toxic to cells at concentration above 1%, the concentration of the compound in DMSO should be at least 10 uM before dilution with aqueous solution. Various concentrations of the compound were tested against HIV-1 in CEM-IW cells. After six days incubation at 37° C. in a 5% carbon dioxide atmosphere, viable cells were analyzed through addition of tetrazolium salt XTT followed by incubation to allow formazan color development. Cell viability was viewed microscopically and detected spectrophotometrically to quantitate formazan production.

In a test against HIV-1(6S)-AZT sensitive, the compound CADA (compound 1) was found active. The $IC_{50}$ index was greater than $5.00 \times 10^{-5}$ M; the $EC_{50}$ was $1.20 \times 10^{-6}$ M; and the $TI_{50}$ (IC/EC) was greater than $2.6 \times 10^{+1}$.

In a second test, the compound from another batch of CADA was confirmed active in a primary screen. The $IC_{50}$ index was greater than $6.00 \times 10^{-6}$M; the $EC_{50}$ was $2.40 \times 10^{-6}$M; and the $TI_{50}$ was greater than $2.50 \times 10^{0}$.

EXAMPLE 2

Testing was carried out as described in Example 1 against additional HIV strains. The compound CADA was active against the following viruses using the indicated cell lines:

IIIB strain of HIV-1/MT-4 cell line

HIV-2/CEM cell line

SIV/MT-4 cell line

AZT—resistant HIV-1/MT-2 and MT-4 cell lines

AZT—sensitive HIV-1/MT-4 cell line

A17, a strain of HIV-1 resistant to most of the non-nucleoside reverse transcriptase inhibitors/MT-2 and MT-4 cell lines, WeJo, a clinical isolate of HIV-1/PBMCs (fresh human peripheral blood mononuclear cells).

The compound was found to be active against these viruses with an $EC_{50}$ of 2uM, a $IC_{50}$ greater than 30 μm and a $TI_{50}$ greater than 15. This means that good activity and low cell toxicity were observed in the micromolar range of concentration of the compound.

EXAMPLE 3

Studies were carried out to determine the mechanism of action of the compounds in the HIV life cycle. At least 16 steps in the HIV life cycle have been identified as possible points for therapeutic intervention, yet all the anti-HIV drugs licensed in the U.S. so far (AZT, ddI and ddC) are nucleoside inhibitors of HIV reverse transcriptase (RT). Another group of antivirals, the bicyclams, are believed to act at an early stage in the retrovirus replicative cycle, apparently inhibiting viral uncoating. The action of other anti-HIVs such as the quinolines is unknown.

The studies were based on activity of the compound against HIV-1 in peripheral blood lymphocytes. The results with different solutions and different batches of the compound confirm that the compound is active at submicromolar levels ($EC_{50}$) and has low cytotoxicity ($IC_{50}$). The results of the studies on the mechanism of reaction are summarized in the Table below:

TABLE 1

|  |  | Batch 1 | | |
|---|---|---|---|---|
|  |  | A | B | Batch 2 |
| PBL/HIV-1 Wejo | $EC_{50}$ (μM) | 0.55 | 0.16 | 0.65 |
| Infection | $IC_{50}$ (μM) | >100 | >100 | >100 |
| Attachment | p 24 based | No Inhibition | | |

TABLE 1-continued

|  |  | Batch 1 | | |
|---|---|---|---|---|
|  |  | A | B | Batch 2 |
| RT activity (rA.dT) | $ID_{50}$ (μM) | No Inhibition | | |
| Time of Action Time Course | LTR/gag | No Inhibition of proviral DNA synthesis | | |
| Protease Activity (rp HPLC) | $ID_{50}$ (μM) | 40 | | |
| Mo-MO/HIV-1 Ba-L Infection | $EC_{50}$ (μM) $IC_{50}$ (μM) | 1.5 (fresh) over 30 (high test) | | |
| Latent Infection | (U1/TNF) | No inhibition | | |

Preliminary mechanism of action studies showed that the compound CADA does not appear to inhibit HIV reverse transcriptase or HIV protease at the concentrations determined to be effective in the in vitro assays. It is believed that the CADA acts prior to the integration of virus into the cellular genome, but it does not appear to inhibit virus attachment or cell fusion.

It was concluded that the mechanism of action of the new compounds is different than those of either of the two classes of AIDS drugs currently in use or in clinical trials (reverse transcriptase and protease inhibitors).

EXAMPLE 4

Additional studies on stability, solubility, formulation and pharmokinetics were carried out. Plasma elimination and urinary recovery from mice following i.v. administeration were examined. Solubility of the compound in human, mouse, rat plasma and plasma ultrafiltrate were examined. Stability of the compound in human urine was determined.

The conclusions of these studies are as follows:

1. The compound is stable in mouse and rat plasma ($t_{1/2}$ greater than 200 hrs) and is stable in pH 4.0 buffer ($t_{1/2}$ 139 hrs) and in human plasma ($t_{1/2}$ 126 hrs).

2. The compound is soluble in human plasma at 37° C. (1–2 ug/mL=2–3uM).

3. The compound can be formulated for animal studies at a concentration of 1.2 uM in a 1:20 mixture of DMSO and normal saline (pH 2.7).

4. The compound is detectable in mouse plasma up to 2 hours after in vivo intravenous administration.

EXAMPLE 5

Additional antiviral testing was carried out to assess the efficacy of the compounds of the invention against human cytomegalovirus (HCMV), herpes simplex virus (HSV), rous sarcoma virus (RSC) and influenza virus (FLU WSN).

Compounds tested were the HCl salts of the products compounds (1), (2) and (12) and non-salt compound (1). The results are summarized in the table below

TABLE 2

|  | $IC_{50}$, ug/mL | | | |
|---|---|---|---|---|
| Virus | 2 · HCl | CADA (1) | 1 · HCl | 12 · HCl |
| HCMV | 5 | >30, >50 | PDR | 3 |
| HSV | 11 | 10, 30 | PDR | 1.5 |

TABLE 2-continued

| | $IC_{50}$, ug/mL | | | |
|---|---|---|---|---|
| Virus | 2 · HCl | CADA (1) | 1 · HCl | 12 · HCl |
| RSV | 4 | >30, >50 PDR | PDR | 4 |
| FLU WSH | >50 | >30, >50 | >50 | 12 |

PDR = poor dose response

The data in the table represents the concentration of compound causing 50% protection against virus.

While not wishing to be bound by any one theory, one hypothesis is that in the mechanism of action of the invention, the drug inhibits retroviral uncoating by binding to a hydrophobic pocket on one of the HIV capsid proteins. A series of hydrophobic compounds, such as disoxaril or Win 51711 are known to inhibit picornavirus replication by this mechanism and various other drugs seem to neutralize rhinoviruses by binding to a specific hydrophobic pocket within the virion capsid protein. The major HIV capsid protein (p24) is a potential target, although it has not been shown that such compounds can be as effective against an enveloped virus as they are against simple icosahedral viruses. Anti-influenza A drugs amantadine and rhimantidine inhibit virus replication by blocking a proton channel associated with capsid protein M2, thereby interfering with virus uncoating.

The bicyclams are the only reported inhibitors of HIV uncoating. CADA superficially resembles bicyclam as a macrocyclic polyamine. CADA's basic tertiary amino group should be protonated at physiologic pH and both compounds could function as metal chelating agents. These similarities with bicyclams are only superficial, however, because the toluenesulfonamide groups of 1 should render it a very weak metal chelator and 1 is much more lipophilic (hydrophobic) than bicyclams which should be polyprotonated a physiologic pH. Although a sulfonamide, CADA is cationic rather than anionic and does not belong to the polyanionic sulfate class of anti-HIV agents that inhibit binding of the virion to target cells.

Inhibition of the HIV enzyme integrase is a second hypothetical mechanism of action consistent with the observation that CADA acts at an early stage of HIV replication. Integrase controls the incorporation of virally transcribed DNA into the host genome, a key step in HIV replication. Many drugs have been found to bind and inhibit HIV-1 integrase in enzymatic in vitro experiments, but none of these compounds prevents HIV replication in intact cells. It is possible that CADA is the first therapeutically active drug operating by integrase inhibition.

Whether CADA is an uncoating inhibitor, an integrase inhibitor or operates by another mechanism, its discovery leads to a new class of drugs complementing inhibitors of reverse transcriptase and protease, used individually or in combination therapy. CADA has a unique activity profile and it operates at an early stage of HIV replication by a mechanism not involving adhesion, fusion or reverse transcriptase inhibition. The discovery shows the potential for a new approach to AIDS chemotherapy. It is likely that the synthesis of hundreds of analogues will produce potent anti-HIV agents with improved solubility and bioavailability.

EXAMPLE 6

Additional antiviral testing was carried out to test the efficacy of compounds of the invention against human cytomegalovirus (HCMV) and another herpesvirus, Varicella Zoster Virus(VZV). The compounds tested were compound (1), the HCl salt of compound (1), Compounds 211, 43, 213 and 214.

The results are summarized in the table below.

TABLE 3

Antiviral Screening Results for Herpesviruses

| | Human Cytomegalovirus[2] | | | Varicella Zoster Virus[3] | | |
|---|---|---|---|---|---|---|
| Compound | $EC_{50}$ | $CC_{50}$ | SI | $EC_{50}$ | $CC_{50}$ | SI |
| CADA (1) | >34 | 133 | <3.9 | 5.3 | 89 | 16.8 |
| 1 · HCl | >160 | >160 | 0 | 3.4 | >160 | >47.1 |
| 211 | >170 | >170 | 0 | 91.7 | >170 | >1.8 |
| 43 | >170 | >170 | 0 | 24.3 | >170 | >7.0 |
| 213 | 3.0 | 167 | 55.6 | 170 | >180 | >1.0 |
| 214 | 2.2 (20.5) | >150 (147) | >68 (7.1) | 25.2 | 68.5 | 2.7 |

[1]Screening system: human foreskin fibroblast cells. $EC_{50}$ values are concentrations ($\mu$M) required to inhibit viral cytopathogenicity by 50%. $CC_{50}$ values are concentrations ($\mu$M) required to inhibit cell proliferation by 50% (cytotoxicity). SI (selectivity index) = $CC_{50}/EC_{50}$. Note: None of the compounds tested showed significant activity against Herpes Simplex virus (HSV type 1 or 2) or Epstein Barr virus (EBV), except for Compound 213, which showed anti-EBV activity ($EC_{50}$ 6.7 $\mu$M; $CC_{50}$ > 180 $\mu$M; SI > 26.9).
[2]Values not in parentheses are results of a semi-automated CPE-inhibition assay for human cytomegalovirus (HCMV). Values in parentheses are from plaque reduction assay.
[3]Results of plaque reduction assay for VZV (Ellen strain).

EXAMPLE 7

Testing was carried out as described in Example 1 against additional HIV strains MB48 and 2h. The results are summarized in the table below.

TABLE 4

| | $ED_{50}$ ($\mu$M)[1] | | |
|---|---|---|---|
| Compound | MB48/MT-2[2] | MD48/HeLa[3] | 2h/PBMC[4] |
| CADA (1) | 0.8 | 0.5 | 0.15 |
| 1 · HCl | 0.2 | 0.1 | 0.15 |
| 211 | 1.9 | 1.5 | 0.5 |
| 43 | 1.8 | 3.5 | 0.5 |
| 004 | 2.6 | 3.5 | 0.5 |

[1]Concentrations required to inhibit viral cytopathogenicity by 50% for HIV strains and cell lines given.
[2]Reverse transcriptase (RT) assay in MT-2 cells.
[3]MAGI assay on HeLa-MAGIC cells (plaque inhibition).
[4]Protein (p24) assay in PBMC cells with 2h, a primary pediatric clinical isolate.

These results show antiviral activity in the submicromolar range.

EXAMPLE 8

The efficacy of intravenously administered CADA-HCl in rabbits during ocular Varicella Zaster Virus (VZV) infection was determined. Intravenous therapy with 5 mg/kg/day CADA-HCl for 11 days was compared with 20 mg/kg/day acyclovir (ACV) intravenous therapy.

Rabbits were bilaterally inoculated with an intrastromal injection of 100 $\mu$L of McKrae strain VZV titer of $10^5$/ml. On day 2 to 3 post inoculation (PI) animals were evaluated and divided into equal groups.

Intravenous therapy of CADA-HCl, acyclovir and placebo saline was initiated immediately after animal grouping and continued through day 11 PI. Two groups received CADA∩HCl intravenous therapy for 9 days, one group at a "low-dose" of 5 mg/kg/day and another group at a "high-dose" of 10 mg/kg/day. Other groups received similar IV therapy with ACV at 20 mg/kg/day and with placebo.

As a result, VZV-induced corneal stromal and iris disease demonstrated a positive response to therapy with CADA-HCl and with ACV. CADA∩HCl at both concentrations was effective in reducing the development of stromal disease. By day 6 PI, acyclovir was intermediate between placebo and low dose CADA-HCl.

Both CADA-HCl and ACV also showed a positive therapeutic response in reducing iris disease development. In efficacy against iris disease (uveitis) CADA-HCl and ACV both showed a positive effect. By day 5 PI, CADA∩HCl was more effective than acyclovir therapy in reducing development of iritis and in speeding resolution of VZV disease.

What is claimed is:

1. A pharmaceutical composition having pharmacological activity comprising a compound of formula I and a pharmaceutically effective carrier:

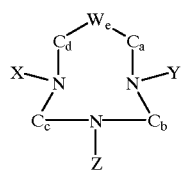

formula I wherein

W is a bridge carbon which has a polar or non-polar side group,

X and Y independently are an aromatic group, an alkyl group, a sulfonyl group or a carbonyl group, said aromatic group is selected from the group consisting of Ar, Ar sulfonyl, Ar carboxy and Ar alkyl, where Ar is an aromatic cyclic or aromatic heterocyclic ring having from five to seven members, said alkyl groups having from one to ten carbons, X and Y are not both an alkyl group so that at least one of X and Y is an aromatic group, a sulfonyl group or a carbonyl group, Z is a group listed for X and Y, a fused aryl moiety having from seven to ten carbons or hydrogen, a, d and e independently are a number from zero to 10, c and b independently are a number from one to 10, and the compound is cyclic or acyclic and includes sufficient hydrogens for a stable molecule.

2. The pharmaceutical composition claim 1 wherein the polar or non-polar side group for W is selected from the group consisting of double-bonded carbon, double-bonded oxygen, hydroxyl, alkyl of one to about 10 carbons, alkoxy of one to about 10 carbons, aryl of about seven to about 10 carbons, halogen, methyl halogen, methylene halide, epoxide, acyl, CH$_2$OH and hydrogen.

3. The pharmaceutical composition of claim 1 wherein the group for X and Y is further substituted with a hydrophilic group.

4. The pharmaceutical composition of claim 1 wherein the group for X and Y is further substituted with NO, NO$_2$, NH$_2$, NHR, NHR$_2$, OH, OR, SH, SR, SOR, SO$_2$R, halo, C(halogen)$_3$,

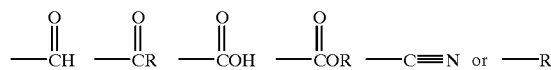

where R is alkyl of C$_{1-10}$.

5. The pharmaceutical composition of claim 1 wherein X and Y are independently

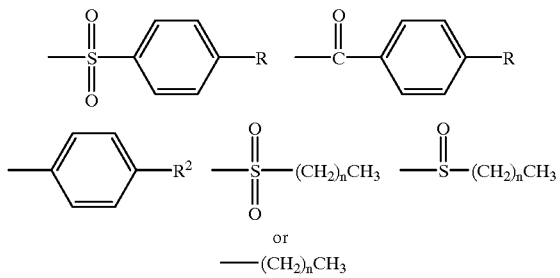

n = zero to nine
R = alkyl of one to 10 carbons
R$^2$ = amino, nitro, sulfhydryl, hydroxy, alkoxy of one to three carbons, acetamino or methyl .

6. The pharmaceutical composition claim 1 wherein c and b are three and a, d and e are independently zero or one.

7. The pharmaceutical composition claim 1 wherein W is ethene, X and Y are both tosyl and Z is benzyl.

8. The pharmaceutical composition claim 1 wherein the compound is

3-Methylene-1,5-ditosyl-1,5,9-triazacyclododecane
9-Benzyl-3-hydroxymethyl-1,5-ditosyl-1,5,9-triazacyclododecane
9-Benzyl-3-chloromethyl-1,5-ditosyl-1,5,9-triazacyclododecane
3-Chloromethyl-1,5-ditosyl-1,5,9-triazacyclododecane
1,5,9-Tritosyl-1,5,9-triazacyclododecane
3-Methylene-1,5,9-tritosyl-1,5,9-triazacyclododecane
3-Hydroxymethyl-1,5,9-tritosyl-1,5,9-triazacyclododecane
3-Chloromethyl-1,5,9-tritosyl-1,5,9-triazacyclododecane
9-Benzyl-3-keto-1,5-ditosyl-1,5,9-triazacyclododecane
9-Benzyl-3-methyl-1,5-ditosyl-1,5,9-triazacyclododecane
9-Benzyl-3-methylene-1,5-ditosyl-1,5,9-triazacyclododecane-9-oxide
9-Acyl-3-methylene-1,5-ditosyl-1,5,9-triazacyclododecane
9-Alkyl-3-methylene-1,5-ditosyl-1,5,9-triazacyclododecane
9-Acyl-3-methylene-1,5-ditosyl-1,5,9-triazacyclododecane epoxide
9-Benzyl-1-formyl-3-methylene-5-tosyl-1,5,9-triazacyclododecane
9-Benzyl-3-methylene-1-tosyl-1,5,9-triazacyclododecane
9-Benzyl-3-methylene-1-acyl-5-tosyl-1,5,9-triazacyclododecane
9-(Ethoxycarbonyl)-3-methylene-1,5-ditosyl-1,5,9-triazacyclododecane
N-Benzylbis(3-benzenesulfonamidopropyl)amine
9-Benzyl-3-methylene-1,5-dibenzenesulfonyl-1,5,9-triazacyclododecane N-Benzylbis[3-(N'-2-propenyltoluenesulfonamido) propyl]amine dihydrogen sulfate N-Benzyl-N-[3-(N'-2-methyl-2-propenyl-toluenesulfonamido)propyl]-N-(3-toluenesulfonamido-propyl)amine dihydrogen sulfate N-Benzylbis[3-(N'-2-methyl-2-propenyltoluenesulfonamido)propyl]amine dihydrogen sulfate; and the compound is in salt or non-salt form.

9. The pharmaceutical composition claim 1 wherein the compound is 9-benzyl-3-methylene-1,5-ditosyl-1,5,9-triazacyclododecane, N-benzylbis(3-toluenesulfonamidopropyl)amine, 3-methylene-1,5-ditosyl-1,5,9-triazacyclododecane, 9-(Ethoxycarbonyl)-3-methylene-1,5-ditosyl-1,5,9-triazacyclododecane, N-Benzylbis(3-benzenesulfonamidopropyl)amine, 9-Benzyl-3-methylene-1,5-dibenzenesulfonyl-1,5,9-triazacyclododecane, N-Benzylbis[3-(N'-2-propenyltoluenesulfonamido) propyl]amine dihydrogen sulfate, N-Benzyl-N-[3-(N'-2-methyl-2-propenyl-toluenesulfonamido)propyl]-N-(3-toluenesulfonamido-propyl)amine dihydrogen sulfate, N-Benzylbis(3-(N'-2-methyl-2-propenyltoluene-sulfonamido)propyllamine dihydrogen sulfate, or salts of these compounds.

10. The pharmaceutical composition of claim 1 wherein the pharmaceutical activity is antiviral.

11. The pharmaceutical composition of claim 10 wherein the virus is a retrovirus, herpesvirus, influenza virus or rous sarcoma virus.

12. The pharmaceutical composition of claim 11 wherein the retrovirus is HIV.

13. The pharmaceutical composition of claim 11 wherein the herpesvirus is Cytomegalovirus or Varicella zoster virus.

14. A compound which is

9-Benzyl-3-keto-1,5-ditosyl-1,5,9-triazacyclododecane

9-Benzyl-3-methyl-1,5-ditosyl-1,5,9-triazacyclododecane

9-Benzyl-3-methylene-1,5-ditosyl-1,5,9-triazacyclododecane-9-oxide

9-Acyl-3-methylene-1,5-ditosyl-1,5,9-triazacyclododecane

9-Alkyl-3-methylene-1,5-ditosyl-1,5,9-triazacyclododecane

9-Acyl-3-methylene-1,5-ditosyl-1,5,9-triazacyclododecane epoxide

9-Benzyl-1-formyl-3-methylene-1,5,9-triazacyclododecane

9-Benzyl-1-formyl-3-methylene-5-tosyl-1,5,9-triazacyclododecane

9-Benzyl-3-methylene-1-tosyl-1,5,9-triazacyclododecane

9-Benzyl-3-methylene-1-acyl-5-tosyl-1,5,9-triazacyclododecane 9-(Ethoxycarbonyl)-3-methylene-1,5-ditosyl-1,5,9-triazacyclododecane N-Benzylbis(3-benzenesulfonamidopropyl)amine 9-Benzyl-3-methylene-1,5-dibenzenesulfonyl-1,5,9-triazacyclododecane N-Benzylbis[3-(N'-2-propenyltoluenesulfonamido) propyl]amine dihydrogen sulfate N-Benzyl-N-[3-(N'-2-methyl-2-propenyltoluenesulfonamido)propyl]-N-(3-toluenesulfonamidopropyl)amine dihydrogen sulfate, or N-Benzylbis[3-(N'2-methyl-2-propenyltoluenesulfonamido)propyl]amine dihydrogen sulfate.

15. The pharmaceutical composition of claim 1 wherein the group for X and Y is further substituted with $NH_2$, NO, $NO_2$, SH, $SO_3H$, OH or $CO_2H$.

* * * * *